(12) United States Patent
McAllister et al.

(10) Patent No.: US 10,865,448 B2
(45) Date of Patent: *Dec. 15, 2020

(54) COMPOSITIONS AND METHODS RELATING TO DENND1A VARIANT 2 AND POLYCYSTIC OVARY SYNDROME

(71) Applicants: THE PENN STATE RESEARCH FOUNDATION, University Park, PA (US); VIRGINIA COMMONWEALTH UNIVERSITY, Richmond, VA (US)

(72) Inventors: Janette M McAllister, Hummelstown, PA (US); Jerome F Strauss, Richmond, VA (US)

(73) Assignees: THE PENN STATE RESEARCH FOUNDATION, University Park, PA (US); VIRGINIA COMMONWEALTH UNIVERSITY, Richmond, VA (US)

( * ) Notice: Subject to any disclaimer, the term of this patent is extended or adjusted under 35 U.S.C. 154(b) by 229 days.

This patent is subject to a terminal disclaimer.

(21) Appl. No.: 15/921,712

(22) Filed: Mar. 15, 2018

(65) Prior Publication Data
US 2018/0216189 A1 Aug. 2, 2018

Related U.S. Application Data

(63) Continuation of application No. 14/402,134, filed as application No. PCT/US2013/031932 on Mar. 15, 2013, now Pat. No. 9,957,567.

(Continued)

(51) Int. Cl.
*G01N 33/53* (2006.01)
*C12Q 1/6883* (2018.01)
*G01N 33/561* (2006.01)

(52) U.S. Cl.
CPC .......... *C12Q 1/6883* (2013.01); *G01N 33/53* (2013.01); *G01N 33/561* (2013.01); *C12Q 2600/112* (2013.01); *C12Q 2600/156* (2013.01)

(58) Field of Classification Search
CPC ............................ G01N 33/53; G01N 33/561
See application file for complete search history.

(56) References Cited

U.S. PATENT DOCUMENTS

2019/0092844 A1* 3/2019 McAllister ............. C07K 16/18

FOREIGN PATENT DOCUMENTS

WO WO-2008067195 A2 * 6/2008 ........... C12Q 1/6883

OTHER PUBLICATIONS

Goodarzi, M.O. et al. Journal of Medical Genetics 49:90 (2012; online Dec. 17, 2011). (Year: 2011).*

* cited by examiner

*Primary Examiner* — Diana B Johannsen
(74) *Attorney, Agent, or Firm* — W&C IP

(57) ABSTRACT

Provided are compositions and methods for use in polycystic ovary syndrome diagnosis (PCOS). The method involves a sample from a subject for a DENND1A Variant 2 mRNA or DENND1A Variant 2 protein to make or aid in a diagnosis of PCOS. Also provided are methods for selecting an individual as a candidate for therapy for polycystic ovary syndrome by testing a biological sample from an individual for DENND1A Variant 2 mRNA or DENND1A Variant 2 protein and designating the individual as a candidate for the PCOS based on determining DENND1A Variant 2 mRNA or DENND1A Variant 2 protein in the sample. Also provided are products for use in aiding diagnosis of PCOS which contain reagents for detecting DENND1A Variant 2

(Continued)

mRNA or DENND1 A Variant 2 protein, and packaging containing printed material describing use and indications for the product.

4 Claims, 7 Drawing Sheets

Specification includes a Sequence Listing.

Related U.S. Application Data

(60) Provisional application No. 61/649,568, filed on May 21, 2012.

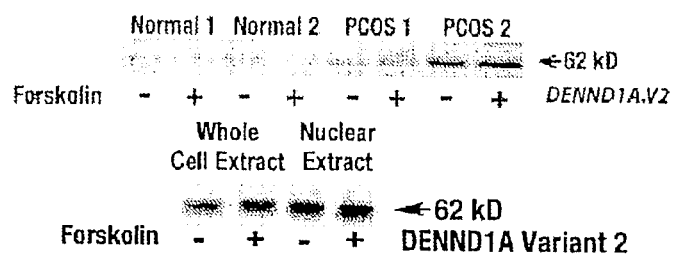
Figure 5A
Figure 5B
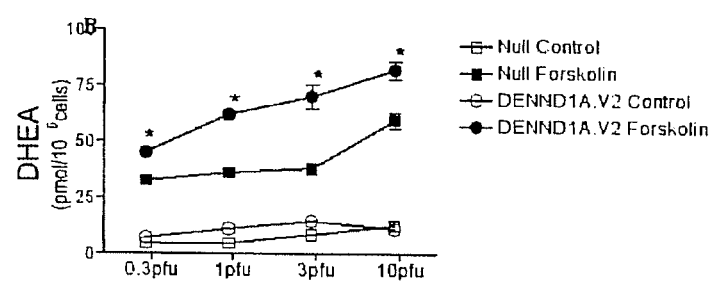
Figure 6A
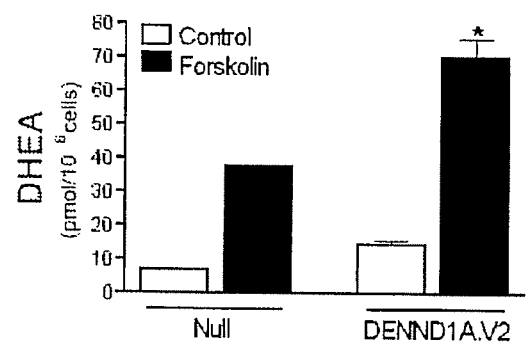
Figure 6B

SEQUENCE LISTING

```
<160> NUMBER OF SEQ ID NOS: 27

<210> SEQ ID NO 1
<211> LENGTH: 2166
<212> TYPE: DNA
<213> ORGANISM: Homo sapiens

<400> SEQUENCE: 1
cgcgcgccgg gcacgcgcgc cggcgaccat ggcgttcgcc gggctggagc gagtacatta      60
acccctggag gcggcggcgg cggcgaggga gcgagcctcg agcgggcggg ccccagcctg     120
agggaaggga ggaaggggcg gggagagcgc cagagggagg ccggtcggcc gcgggcgggc     180
gggcagcgca gcgccgagcg gggcccgcgg gcccatgagg aggcctgggg accatgggct     240
ccaggatcaa gcagaatcca gagaccacat ttgaagtata tgttgaagtg gcctatccca     300
ggacaggtgg cactctttca gatcctgagg tgcagaggca attcccggag gactacagtg     360
accaggaagt tctacagact ttgaccaagt tttgtttccc cttctatgtg gacagcctca     420
cagttagcca agttggccag aacttcacat tcgtgctcac tgacattgac agcaaacaga     480
gattcgggtt ctgccgctta tcttcaggag cgaagagctg cttctgtatc ttaagctatc     540 tccoctggtt cgaggtattt tataagctgc ttaacatcct ggcagattac acgacaaaaa     600
gacaggaaaa tcagtggaat gagcttcttg aaactctgca caaacttccc atccctgacc     660
caggagtgtc tgtccatctc agcgtgcatt cttattttac tgtgcctgat accagagaac     720
ttcccagcat acctgagaat agaaatctga cagaatattt tgtggctgtg gatgttaaca     780
acatgttgca tctgtacgcc agtatgctgt acgaacgccg gatactcatc atttgcagca     840
aactcagcac tctgactgcc tgcatccacg ggtctgcggc gatgctctac cccatgtact     900
ggcagcacgt gtacatcccc gtgctgccgc cgcatctgct ggactactgc tgtgctccca     960
```

-continued

```
tgccctacct cataggaatc catttaagtt taatggagaa agtcagaaac atggccctgg    1020
atgatgtcgt gatcctgaat gtggacacca cacccctgga aacccccttc gatgacctcc    1080
agagcctccc aaacgacgtg atctcttccc tgaagaacag gctgaaaaag gtctccacaa    1140
ccactgggga tggtgtggcc agagcgttcc tcaaggccca ggctgctttc ttcggtagct    1200
accgaaacgc tctgaaaatc gagccggagg agccgatcac tttctgtgag aagccttcg    1260
tgtcccacta ccgctccgga gccatgaggc agttcctgca gaacgccaca cagctgcagc    1320
tcttcaagca gtttattgat ggtcgattag atcttctcaa ttccggcgaa ggtttcagtg    1380
atgttttga agaggaaatc aacatgggcg agtacgctgg cagtgacaaa ctgtaccatc    1440
agtggctctc cactgtccgg aaaggaagtg gagcaattct gaatactgta aagaccaaag    1500
caaatccggc catgaagact gtctacaagt tcgcaaaaga tcatgcaaaa atgggaataa    1560
aagaggtgaa aaaccgcttg aagcaaaagg acattgccga gaatggctgc gcccccaccc    1620
cagaagagca gctgccaaag actgcaccgt ccccactggt ggaggccaag gaccccaagc    1680
tccgagaaga ccggcggcca atcacagtcc actttggaca ggtgcgccca cctcgtccac    1740
atgttgttaa gagaccaaag agcaacatcg cagtggaagg ccggaggacg tctgtgccga    1800
gccctgagca aaacaccatt gcaacaccag ctacactcca catcctacag aaaagcatta    1860
cccattttgc ggccaagttc ccgacgagag gctggacctc ttcatcacat tgacttacgc    1920
cgttgctttt ccagactggg cagaggggct gacttcgcag tgtgtgccaa agagccggtg    1980
tctgataatc ccatttttcct gcttatcacc tgaactgtgt cagtatcact tttagttttg    2040
ttggttggtt ggtttgttgt tgtttaata tgccctgttt tctacttctg ttggaaaata    2100
tttggggttg aaataaacca gtgggagcat ggaaaaaaaa aaaaaaaaa aaaaaaaaa    2160
aaaaaa                                                               2166
```

<210> SEQ ID NO 2
<211> LENGTH: 559
<212> TYPE: PRT
<213> ORGANISM: Homo sapiens

<400> SEQUENCE: 2

```
Met Gly Ser Arg Ile Lys Gln Asn Pro Glu Thr Thr Phe Glu Val Tyr
1               5                   10                  15

Val Glu Val Ala Tyr Pro Arg Thr Gly Gly Thr Leu Ser Asp Pro Glu
            20                  25                  30

Val Gln Arg Gln Phe Pro Glu Asp Tyr Ser Asp Gln Glu Val Leu Gln
        35                  40                  45

Thr Leu Thr Lys Phe Cys Phe Pro Phe Tyr Val Asp Ser Leu Thr Val
    50                  55                  60

Ser Gln Val Gly Gln Asn Phe Thr Phe Val Leu Thr Asp Ile Asp Ser
65                  70                  75                  80

Lys Gln Arg Phe Gly Phe Cys Arg Leu Ser Ser Gly Ala Lys Ser Cys
                85                  90                  95

Phe Cys Ile Leu Ser Tyr Leu Pro Trp Phe Glu Val Phe Tyr Lys Leu
            100                 105                 110

Leu Asn Ile Leu Ala Asp Tyr Thr Thr Lys Arg Gln Glu Asn Gln Trp
        115                 120                 125

Asn Glu Leu Leu Glu Thr Leu His Lys Leu Pro Ile Pro Asp Pro Gly
    130                 135                 140

Val Ser Val His Leu Ser Val His Ser Tyr Phe Thr Val Pro Asp Thr
```

-continued

```
           145                 150                 155                 160
     Arg Glu Leu Pro Ser Ile Pro Glu Asn Arg Asn Leu Thr Glu Tyr Phe
                     165                 170                 175

Val Ala Val Asp Val Asn Asn Met Leu His Leu Tyr Ala Ser Met Leu
                     180                 185                 190

Tyr Glu Arg Arg Ile Leu Ile Ile Cys Ser Lys Leu Ser Thr Leu Thr
                     195                 200                 205

Ala Cys Ile His Gly Ser Ala Ala Met Leu Tyr Pro Met Tyr Trp Gln
         210                 215                 220

His Val Tyr Ile Pro Val Leu Pro Pro His Leu Leu Asp Tyr Cys Cys
     225                 230                 235                 240

Ala Pro Met Pro Tyr Leu Ile Gly Ile His Leu Ser Leu Met Glu Lys
                     245                 250                 255

Val Arg Asn Met Ala Leu Asp Asp Val Ile Leu Asn Val Asp Thr
                 260                 265                 270

Asn Thr Leu Glu Thr Pro Phe Asp Asp Leu Gln Ser Leu Pro Asn Asp
                 275                 280                 285

Val Ile Ser Ser Leu Lys Asn Arg Leu Lys Lys Val Ser Thr Thr Thr
         290                 295                 300

Gly Asp Gly Val Ala Arg Ala Phe Leu Lys Ala Gln Ala Ala Phe Phe
     305                 310                 315                 320

Gly Ser Tyr Arg Asn Ala Leu Lys Ile Glu Pro Glu Pro Ile Thr
                     325                 330                 335

Phe Cys Glu Glu Ala Phe Val Ser His Tyr Arg Ser Gly Ala Met Arg
                     340                 345                 350

Gln Phe Leu Gln Asn Ala Thr Gln Leu Gln Leu Phe Lys Gln Phe Ile
                 355                 360                 365

Asp Gly Arg Leu Asp Leu Asn Ser Gly Glu Gly Phe Ser Asp Val
             370                 375                 380

Phe Glu Glu Glu Ile Asn Met Gly Glu Tyr Ala Gly Ser Asp Lys Leu
     385                 390                 395                 400

Tyr His Gln Trp Leu Ser Thr Val Arg Lys Gly Ser Gly Ala Ile Leu
                     405                 410                 415

Asn Thr Val Lys Thr Lys Ala Asn Pro Ala Met Lys Thr Val Tyr Lys
                     420                 425                 430

Phe Ala Lys Asp His Ala Lys Met Gly Ile Lys Glu Val Lys Asn Arg
                 435                 440                 445

Leu Lys Gln Lys Asp Ile Ala Glu Asn Gly Cys Ala Pro Thr Pro Glu
     450                 455                 460

Glu Gln Leu Pro Lys Thr Ala Pro Ser Pro Leu Val Glu Ala Lys Asp
     465                 470                 475                 480

Pro Lys Leu Arg Glu Asp Arg Pro Ile Thr Val His Phe Gly Gln
                     485                 490                 495

Val Arg Pro Pro Arg Pro His Val Val Lys Arg Pro Lys Ser Asn Ile
                 500                 505                 510

Ala Val Glu Gly Arg Arg Thr Ser Val Pro Ser Pro Glu Gln Asn Thr
             515                 520                 525

Ile Ala Thr Pro Ala Thr Leu His Ile Leu Gln Lys Ser Ile Thr His
             530                 535                 540

Phe Ala Ala Lys Phe Pro Thr Arg Gly Trp Thr Ser Ser Ser His
     545                 550                 555

<210> SEQ ID NO 3
```

```
<211> LENGTH: 5041
<212> TYPE: DNA
<213> ORGANISM: Homo sapiens

<400> SEQUENCE: 3
cgcgcgccgg gcacgcgcgc cggcgaccat ggcgttcgcc gggctggagc gagtacatta      60 accccctggag gcggcggcgg cggcgaggga gcgagcctcg agcgggcggg ccccagcctg    120
agggaaggga ggaaggggcg gggagagcgc cagagggagg ccggtcggcc gcgggcgggc    180
gggcagcgca gcgccgagcg gggcccgcgg gcccatgagg aggcctgggg accatgggct    240
ccaggatcaa gcagaatcca gagaccacat ttgaagtata tgttgaagtg cctatcccca    300
ggacaggtgg cactctttca gatcctgagg tgcagaggca attcccggag gactacagtg    360
accaggaagt tctacagact ttgaccaagt tttgtttccc cttctatgtg gacagcctca    420
cagttagcca agttggccag aacttcacat tcgtgctcac tgacattgac agcaaacaga    480
gattcgggtt ctgccgctta tcttcaggag cgaagagctg cttctgtatc ttaagctatc    540 tccccctggtt cgaggtattt tataagctgc ttaacatcct ggcagattac acgacaaaaa    600
gacaggaaaa tcagtggaat gagcttcttg aaactctgca caaacttccc atccctgacc    660
caggagtgtc tgtccatctc agcgtgcatt cttattttac tgtgcctgat accagagaac    720
ttcccagcat acctgagaat agaaatctga cagaatattt tgtggctgtg atgttaaca    780 acatgttgca tctgtacgcc agtatgctgt acgaacgccg gatactcatc atttgcagca    840
aactcagcac tctgactgcc tgcatccacg ggtctgcggc gatgctctac cccatgtact    900
ggcagcacgt gtacatcccc gtgctgccgc cgcatctgct ggactactgc tgtgctccca    960
tgccctacct cataggaatc catttaagtt taatggagaa agtcagaaac atggccctgg   1020
atgatgtcgt gatcctgaat gtggacacca acccctgga acccccttc gatgacctcc   1080 agagcctccc aaacgacgtg atctcttccc tgaagaacag gctgaaaaag gtctccacaa   1140
ccactgggga tggtgtggcc agagcgttcc tcaaggccca ggctgctttc ttcggtagct   1200
accgaaacgc tctgaaaatc gagccggagg agccgatcac tttctgtgag gaagccttcg   1260
tgtcccacta ccgctccgga gccatgaggc agttcctgca gaacgccaca cagctgcagc   1320
tcttcaagca gtttattgat ggtcgattag atcttctcaa ttccggcgaa ggtttcagtg   1380
atgtttttga gaggaaatc aacatggggcg agtacgctgg cagtgacaaa ctgtaccatc   1440
agtggctctc cactgtccgg aaaggaagtg gagcaattct gaatactgta aagaccaaag   1500
caaatccggc catgaagact gtctacaagt tcgcaaaaga tcatgcaaaa atgggaataa   1560
aagaggtgaa aaaccgcttg aagcaaaagg acattgccga gaatggctgc gcccccaccc   1620
cagaagagca gctgccaaag actgcaccgt ccccactggt ggaggccaag gaccccaagc   1680
tccgagaaga ccggcggcca atcacagtcc actttggaca ggtgcgccca cctcgtccac   1740
atgttgttaa gagaccaaag agcaacatcg cagtggaagg ccggaggacg tctgtgccga   1800
gccctgagca gccgcagccg tatcggacac tcagggagtc agacagcgcg gaaggcgacg   1860
aggcagagag tccagagcag caagtgcgga agtccacagg ccctgtccca gctccccctg   1920
accgggctgc cagcatcgac cttctggaag acgtcttcag caacctggac atggaggccg   1980
cactgcagcc actgggccag gccaagagct tagaggacct tcgtgccccc aaagacctga   2040
gggagcagcc agggacctttt gactatcaga ggctggatct gggcgggagt gagaggagcc   2100
gcggggtgac agtggccttg aagcttaccc accccgtacaa caagctctgg agcctgggcc   2160
aggacgacat ggccatcccc agcaagcccc cagctgcctc ccctgagaag ccctcggccc   2220
```

```
tgctcgggaa ctccctggcc ctgcctcgaa ggccccagaa ccgggacagc atcctgaacc    2280
ccagtgacaa ggaggaggtg cccacccta ctctgggcag catcaccatc ccccggcccc     2340
aaggcaggaa gaccccagag ctgggcatcg tgcctccacc gcccattccc cgcccggcca    2400
agctccaggc tgccggcgcc gcacttggtg acgtctcaga gcggctgcag acggatcggg    2460
acaggcgagc tgccctgagt ccagggctcc tgcctggtgt tgtccccaa ggccccactg     2520 aactgctcca gccgctcagc cctggccccg gggctgcagg cacgagcagt gacgccctgc    2580
tcgccctcct ggacccgctc agcacagcct ggtcaggcag caccctcccg tcacgccccg    2640
ccaccccgaa tgtagccacc ccattcaccc cccaattcag cttccccct gcagggacac     2700 ccacccatt cccacagcca ccactcaacc cctttgtccc atccatgcca gcagccccac     2760
ccaccctgcc cctggtctcc acaccagccg ggcctttcgg ggcccctcca gcttccctgg    2820
ggccggcttt tgcgtccggc tcctgctgt ccagtgctgg cttctgtgcc cctcacaggt     2880
ctcagcccaa cctctccgcc ctctccatgc caacctctt tggccagatg cccatgggca     2940
cccacacgag cccctacag ccgctgggtc cccagcagt tgccccgtcg aggatccgaa      3000
cgttgcccct ggcccgctca gtgccaggg ctgctgagac caagcagggg ctggccctga    3060
ggcctggaga ccccccgctt ctgcctccca ggcccctca aggcctggag ccaacactgc     3120
agccctctgc tcctcaacag gccagagacc cctttgagga tttgttacag aaaaccaagc    3180
aagacgtgag cccgagtccg gccctggccc cggccccaga ctcggtggag cagctcagga    3240
agcagtggga gaccttcgag tgagccgggc cctgagggtg ggggatgcac cgaggcccga    3300
gggtccgtcc actgctgcgg ttccgaggct ccccgccac tctctctctg cccaggttct     3360
gctggtggga agggatggga cccctctctg ctgcccctc ctcccctcca cactgcccat     3420
ctctgatgtc tggccctggg gaatggcacc agttccagcc tgggaatcaa cccagttcct    3480
gagtgcccat cccaccccgc ggttgcctct cctcggcacc cttgattggg ttttgcacta    3540
aagaggtcag ctgggccaat gatattgctc cagaccgagt cctacccacc ttcccccgga   3600
agtgtcccaa gaggctccga aggcctcccc tccgagccca gctctcctgt ctcctccaca    3660
gccaggccct gcacgccac ctcctcggac acaggtgaca gggttaccct ccagtttgag     3720
ctcatctgca cgagacacag gtagcttggg gttgaagtta ggactcctcc tgggctggag    3780
gatttacctg gtggggcact tccagactgt ttctagcaat atacacacac gttctttcct    3840
gtgtcttcac cccaaaactt cagttgattc tgacctggga ggatctgggg accagggggt    3900
cttgggctgc cttgtgatac acagcccag ccaccctgca cggggctgc gagcaccagc      3960 aactttgatt tatagaagga aaatggaaac ccccatctga gtattttggg aggagccccc    4020
agccctcatc cagctctggc acgctgatac ctccaggtac tcccctcact gtcaaagctg    4080
gggctcagcc tcttgtcatc tggagctttg tgggcaaagc tgagaagctg caacccagat    4140
ttcaacccaa aaaggtcaag ctgaatgcct cagactgatg tggaaggcag ctggccttcc    4200
tgggttggaa cgaggcagtg gccctgagcc ccttctccag ggccaggtag aaaggacaaa    4260
cttggtctct gcctcgggga agcaggagga gggctagaag ccagtccctc cccacctgcc    4320
cagagctcca ggccagcaca gaaattcctg aggccaacgt caccaaagtt agattgaatg    4380
tttattatct ttctttttcc tttttacctt attgatttga tgaatcttga aatggattca    4440
tttccataaa ccaagttaaa gtatggcccg accatttaag aaaacaacca tctgagacac    4500
gcaggaaatt gtgagcattt cgacccgagc tctcatttcc tatttgtgaa gggtcagaca    4560
```

```
cagtctaccc agggtgtct gggggacaag ggggtctctg agatgtcac ccagggagcc    4620 ccctctatgt ctgagaggct gccactgctg cacatgctca gtgaggcttg gcggccatcc    4680
tggcacatgg ctcttcctgg gtcaaccgtg acctgtctgg ctcaggaatg ggctctggct    4740
gctgggggag ccgtgtcact cctgggccat gggggcacct cctgggcact taggtgtttc    4800
agcatagatt ccagtttcgc accctgggca gaccccagg ccccatccgg gatagggcag    4860
aggaggtgct ggcggcccca gggaaggagg gtgtgtaccc caaggccccc tggctgtgct    4920
gaggggctgg ggtgagcgct ccatgttcac atgagcactg ctgcctcttc acttgtggga    4980 cttttttgcaa acccaaggat gaactttgtg tgcattcaat aaaatcatct tggggaagag    5040
g                                                                    5041
```

<210> SEQ ID NO 4
<211> LENGTH: 1009
<212> TYPE: PRT
<213> ORGANISM: Homo sapiens

<400> SEQUENCE: 4

```
Met Gly Ser Arg Ile Lys Gln Asn Pro Glu Thr Thr Phe Glu Val Tyr
1               5                   10                  15

Val Glu Val Ala Tyr Pro Arg Thr Gly Gly Thr Leu Ser Asp Pro Glu
            20                  25                  30

Val Gln Arg Gln Phe Pro Glu Asp Tyr Ser Asp Gln Glu Val Leu Gln
        35                  40                  45

Thr Leu Thr Lys Phe Cys Phe Pro Phe Tyr Val Asp Ser Leu Thr Val
    50                  55                  60

Ser Gln Val Gly Gln Asn Phe Thr Phe Val Leu Thr Asp Ile Asp Ser
65                  70                  75                  80

Lys Gln Arg Phe Gly Phe Cys Arg Leu Ser Ser Gly Ala Lys Ser Cys
                85                  90                  95

Phe Cys Ile Leu Ser Tyr Leu Pro Trp Phe Glu Val Phe Tyr Lys Leu
            100                 105                 110

Leu Asn Ile Leu Ala Asp Tyr Thr Thr Lys Arg Gln Glu Asn Gln Trp
        115                 120                 125

Asn Glu Leu Leu Glu Thr Leu His Lys Leu Pro Ile Pro Asp Pro Gly
    130                 135                 140

Val Ser Val His Leu Ser Val Ser Tyr Phe Thr Val Pro Asp Thr
145                 150                 155                 160

Arg Glu Leu Pro Ser Ile Pro Glu Asn Arg Asn Leu Thr Glu Tyr Phe
                165                 170                 175

Val Ala Val Asp Val Asn Asn Met Leu His Leu Tyr Ala Ser Met Leu
            180                 185                 190

Tyr Glu Arg Arg Ile Leu Ile Cys Ser Lys Leu Ser Thr Leu Thr
        195                 200                 205

Ala Cys Ile His Gly Ser Ala Ala Met Leu Tyr Pro Met Tyr Trp Gln
    210                 215                 220

His Val Tyr Ile Pro Val Leu Pro Pro His Leu Leu Asp Tyr Cys Cys
225                 230                 235                 240

Ala Pro Met Pro Tyr Leu Ile Gly Ile His Leu Ser Leu Met Glu Lys
                245                 250                 255

Val Arg Asn Met Ala Leu Asp Asp Val Val Ile Leu Asn Val Asp Thr
            260                 265                 270

Asn Thr Leu Glu Thr Pro Phe Asp Asp Leu Gln Ser Leu Pro Asn Asp
        275                 280                 285
```

```
Val Ile Ser Ser Leu Lys Asn Arg Leu Lys Val Ser Thr Thr Thr
        290                 295                 300

Gly Asp Gly Val Ala Arg Ala Phe Leu Lys Ala Gln Ala Ala Phe Phe
305                 310                 315                 320

Gly Ser Tyr Arg Asn Ala Leu Lys Ile Glu Pro Glu Glu Pro Ile Thr
                325                 330                 335

Phe Cys Glu Glu Ala Phe Val Ser His Tyr Arg Ser Gly Ala Met Arg
                340                 345                 350

Gln Phe Leu Gln Asn Ala Thr Gln Leu Gln Leu Phe Lys Gln Phe Ile
        355                 360                 365

Asp Gly Arg Leu Asp Leu Leu Asn Ser Gly Gly Phe Ser Asp Val
370                 375                 380

Phe Glu Glu Glu Ile Asn Met Gly Glu Tyr Ala Gly Ser Asp Lys Leu
385                 390                 395                 400

Tyr His Gln Trp Leu Ser Thr Val Arg Lys Gly Ser Gly Ala Ile Leu
                405                 410                 415

Asn Thr Val Lys Thr Lys Ala Asn Pro Ala Met Lys Thr Val Tyr Lys
                420                 425                 430

Phe Ala Lys Asp His Ala Lys Met Gly Ile Lys Glu Val Lys Asn Arg
        435                 440                 445

Leu Lys Gln Lys Asp Ile Ala Glu Asn Gly Cys Ala Pro Thr Pro Glu
450                 455                 460

Glu Gln Leu Pro Lys Thr Ala Pro Ser Pro Leu Val Glu Ala Lys Asp
465                 470                 475                 480

Pro Lys Leu Arg Glu Asp Arg Pro Ile Thr Val His Phe Gly Gln
                485                 490                 495

Val Arg Pro Pro Arg Pro His Val Val Lys Arg Pro Lys Ser Asn Ile
                500                 505                 510

Ala Val Glu Gly Arg Arg Thr Ser Val Pro Ser Pro Glu Gln Pro Gln
        515                 520                 525

Pro Tyr Arg Thr Leu Arg Glu Ser Asp Ser Ala Glu Gly Asp Glu Ala
530                 535                 540

Glu Ser Pro Glu Gln Gln Val Arg Lys Ser Thr Gly Pro Val Pro Ala
545                 550                 555                 560

Pro Pro Asp Arg Ala Ala Ser Ile Asp Leu Leu Glu Asp Val Phe Ser
                565                 570                 575

Asn Leu Asp Met Glu Ala Ala Leu Gln Pro Leu Gly Gln Ala Lys Ser
                580                 585                 590

Leu Glu Asp Leu Arg Ala Pro Lys Asp Leu Arg Glu Gln Pro Gly Thr
        595                 600                 605

Phe Asp Tyr Gln Arg Leu Asp Leu Gly Gly Ser Glu Arg Ser Arg Gly
610                 615                 620

Val Thr Val Ala Leu Lys Leu Thr His Pro Tyr Asn Lys Leu Trp Ser
625                 630                 635                 640

Leu Gly Gln Asp Asp Met Ala Ile Pro Ser Lys Pro Pro Ala Ala Ser
                645                 650                 655

Pro Glu Lys Pro Ser Ala Leu Leu Gly Asn Ser Leu Ala Leu Pro Arg
                660                 665                 670

Arg Pro Gln Asn Arg Asp Ser Ile Leu Asn Pro Ser Asp Lys Glu Glu
        675                 680                 685

Val Pro Thr Pro Thr Leu Gly Ser Ile Thr Ile Pro Arg Pro Gln Gly
690                 695                 700
```

-continued

Arg Lys Thr Pro Glu Leu Gly Ile Val Pro Pro Pro Ile Pro Arg
705                 710                 715                 720

Pro Ala Lys Leu Gln Ala Ala Gly Ala Ala Leu Gly Asp Val Ser Glu
            725                 730                 735

Arg Leu Gln Thr Asp Arg Asp Arg Arg Ala Ala Leu Ser Pro Gly Leu
            740                 745                 750

Leu Pro Gly Val Val Pro Gln Gly Pro Thr Glu Leu Leu Gln Pro Leu
        755                 760                 765

Ser Pro Gly Pro Gly Ala Ala Gly Thr Ser Ser Asp Ala Leu Leu Ala
        770                 775                 780

Leu Leu Asp Pro Leu Ser Thr Ala Trp Ser Gly Ser Thr Leu Pro Ser
785                 790                 795                 800

Arg Pro Ala Thr Pro Asn Val Ala Thr Pro Phe Thr Pro Gln Phe Ser
            805                 810                 815

Phe Pro Pro Ala Gly Thr Pro Thr Pro Phe Pro Gln Pro Pro Leu Asn
            820                 825                 830

Pro Phe Val Pro Ser Met Pro Ala Ala Pro Pro Thr Leu Pro Leu Val
        835                 840                 845

Ser Thr Pro Ala Gly Pro Phe Gly Ala Pro Ala Ser Leu Gly Pro
        850                 855                 860

Ala Phe Ala Ser Gly Leu Leu Leu Ser Ser Ala Gly Phe Cys Ala Pro
865                 870                 875                 880

His Arg Ser Gln Pro Asn Leu Ser Ala Leu Ser Met Pro Asn Leu Phe
            885                 890                 895

Gly Gln Met Pro Met Gly Thr His Thr Ser Pro Leu Gln Pro Leu Gly
            900                 905                 910

Pro Pro Ala Val Ala Pro Ser Arg Ile Arg Thr Leu Pro Leu Ala Arg
        915                 920                 925

Ser Ser Ala Arg Ala Ala Glu Thr Lys Gln Gly Leu Ala Leu Arg Pro
        930                 935                 940

Gly Asp Pro Pro Leu Leu Pro Pro Arg Pro Pro Gln Gly Leu Glu Pro
945                 950                 955                 960

Thr Leu Gln Pro Ser Ala Pro Gln Gln Ala Arg Asp Pro Phe Glu Asp
            965                 970                 975

Leu Leu Gln Lys Thr Lys Gln Asp Val Ser Pro Ser Pro Ala Leu Ala
            980                 985                 990

Pro Ala Pro Asp Ser Val Glu Gln Leu Arg Lys Gln Trp Glu Thr Phe
        995                 1000                1005

Glu

<210> SEQ ID NO 5
<211> LENGTH: 356
<212> TYPE: DNA
<213> ORGANISM: Homo sapiens

<400> SEQUENCE: 5
aaacaccatt gcaacaccag ctacactcca catcctacag aaaagcatta cccatttgc        60 ggccaagttc ccgacgagag gctggaccte ttcatcacat tgacttacgc cgttgctttt     120
ccagactggg cagaggggct gacttcgcag tgtgtgccaa agagccggtg tctgataatc     180
ccatttccct gcttatcacc tgaactgtgt cagtatcact tttagttttg ttggttggtt     240
ggtttgttgt tgtttaaata tgccctgttt tctacttctg ttggaaaata tttgggttg      300 aaataaacca gtgggagcat ggaaaaaaaa aaaaaaaaaa aaaaaaaaaa aaaaaa          356

<210> SEQ ID NO 6
<211> LENGTH: 322
<212> TYPE: DNA
<213> ORGANISM: Homo sapiens

<400> SEQUENCE: 6

```
aaacaccatt gcaacaccag ctacactcca catcctacag aaaagcatta cccattttgc      60
ggccaagttc ccgacgagag gctggacctc ttcatcacat tgacttacgc cgttgctttt     120
ccagactggg cagaggggct gacttcgcag tgtgtgccaa agagccggtg tctgataatc     180 ccatttttcct gcttatcacc tgaactgtgt cagtatcact tttagttttg ttggttggtt    240
ggtttgttgt ttgtttaata tgccctgttt tctacttctg ttggaaaata tttggggttg     300
aaataaacca gtgggagcat gg                                              322
```

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7

```
gggctgactt cgcagtgtgt                                                  20
```

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8

```
acagttcagg tgataagcag gaaa                                             24
```

<210> SEQ ID NO 9
<211> LENGTH: 28
<212> TYPE: DNA
<213> ORGANISM: Artificial Sequence
<220> FEATURE:
<223> OTHER INFORMATION: Artificial sequence
<220> FEATURE:
<221> NAME/KEY: misc_feature
<223> OTHER INFORMATION: n is a secondary quenching moiety
<220> FEATURE:
<221> NAME/KEY: misc_feature
<222> LOCATION: (10)..(10)
<223> OTHER INFORMATION: n is a, c, g, or t

<400> SEQUENCE: 9

```
ccaaagagcn cggtgtctga taatccca                                         28
```

<210> SEQ ID NO 10
<211> LENGTH: 33
<212> TYPE: PRT
<213> ORGANISM: Homo sapiens

<400> SEQUENCE: 10

Asn Thr Ile Ala Thr Pro Ala Thr Leu His Ile Leu Gln Lys Ser Ile
1               5                   10                  15

Thr His Phe Ala Ala Lys Phe Pro Thr Arg Gly Trp Thr Ser Ser Ser
            20                  25                  30

His

```
<210> SEQ ID NO 11
<211> LENGTH: 21
<212> TYPE: PRT
<213> ORGANISM: Homo sapiens

<400> SEQUENCE: 11

Gln Lys Ser Ile Thr His Phe Ala Ala Lys Phe Pro Thr Arg Gly Trp
1               5                   10                  15

Thr Ser Ser Ser His
            20

<210> SEQ ID NO 12
<211> LENGTH: 23
<212> TYPE: DNA
<213> ORGANISM: Artificial Sequence
<220> FEATURE:
<223> OTHER INFORMATION: Artificial sequence

<400> SEQUENCE: 12
cgacgagagg ctggacctct tac                                            23

<210> SEQ ID NO 13
<211> LENGTH: 23
<212> TYPE: DNA
<213> ORGANISM: Artificial Sequence
<220> FEATURE:
<223> OTHER INFORMATION: Artificial sequence

<400> SEQUENCE: 13
cctcttcatc acattgactt acg                                            23

<210> SEQ ID NO 14
<211> LENGTH: 19
<212> TYPE: DNA
<213> ORGANISM: Artificial Sequence
<220> FEATURE:
<223> OTHER INFORMATION: Artificial sequence

<400> SEQUENCE: 14
ctcttcatca cattgactt                                                 19

<210> SEQ ID NO 15
<211> LENGTH: 212
<212> TYPE: DNA
<213> ORGANISM: Artificial Sequence
<220> FEATURE:
<223> OTHER INFORMATION: Artificial sequence

<400> SEQUENCE: 15
cgttgctttt ccagactggg cagaggggct gacttcgcag tgtgtgccaa agagccggtg    60
tctgataatc ccattttcct gcttatcacc tgaactgtgt cagtatcact tttagttttg   120
ttggttggtt ggtttgttgt ttgtttaata tgccctgttt tctacttctg ttggaaaata   180
tttggggttg aaataaacca gtgggagcat gg                                 212

<210> SEQ ID NO 16
<211> LENGTH: 27
<212> TYPE: DNA
<213> ORGANISM: Artificial Sequence
<220> FEATURE:
<223> OTHER INFORMATION: Synthetic primer

<400> SEQUENCE: 16
ggattcattt ccataaacca agttaaa                                        27
```

```
<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
cacaatttcc tgcgtgtctc a                                              21

<210> SEQ ID NO 18
<211> LENGTH: 30
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: n is a fluorophore or secondary quenching
      moiety
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 18
natggcccga nccatttaag aaaacaacca                                     30

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
ggcctcaaat ggcaactcta ga                                             22

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
cttctgatcg ccatccttga a                                              21

<210> SEQ ID NO 21
<211> LENGTH: 27
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: n is a fluorophore
<220> FEATURE:
<221> NAME/KEY: misc_feature
<222> LOCATION: (1)..(1)
<223> OTHER INFORMATION: n is a, c, g, or t

<400> SEQUENCE: 21
ntcgcgtcca acaaccgtaa gggtatc                                        27
```

```
<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22
cacggcactg attttcagtt c                                              21

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
tcttgctgcc agtctggact                                                20

<210> SEQ ID NO 24
<211> LENGTH: 26
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: n is a fluorophore
<220> FEATURE:
<221> NAME/KEY: misc_feature
<222> LOCATION: (1)..(1)
<223> OTHER INFORMATION: n is a, c, g, or t

<400> SEQUENCE: 24
ntgtgcacag gagccaagag tgaaga                                         26

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
gtctcccatc caagtactaa cc                                             22

<210> SEQ ID NO 26
<211> LENGTH: 28
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: n is a fluorophore or secondary quenching
      moiety
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 26
ntctcgtctg natctcggaa gctaagca                                       28
```

```
<210> SEQ ID NO 27
<211> LENGTH: 50
<212> TYPE: PRT
<213> ORGANISM: Artificial Sequence
<220> FEATURE:
<223> OTHER INFORMATION: Synthetic sequence

<400> SEQUENCE: 27

Pro Gly Val Ser Val His Leu Ser Val His Ser Tyr Phe Thr Val Pro
1               5                   10                  15

Asp Thr Arg Glu Leu Pro Ser Ile Pro Glu Asn Arg Asn Leu Thr Glu
            20                  25                  30

Tyr Phe Val Ala Val Asp Val Asn Asn Met Leu His Leu Tyr Ala Ser
        35                  40                  45

Met Leu
    50
```

COMPOSITIONS AND METHODS RELATING TO DENND1A VARIANT 2 AND POLYCYSTIC OVARY SYNDROME

CROSS REFERENCE TO RELATED APPLICATIONS

This application claims priority to U.S. Provisional application No. 61/649,568, filed on May 21, 2012, the disclosure of which is incorporated herein by reference.

STATEMENT REGARDING FEDERALLY SPONSORED RESEARCH

This invention was made with government support under Grant Nos. HD033852, HD034449, and HD058300, awarded by the National Institutes of Health. The Government has certain rights in the invention.

FIELD OF THE INVENTION

The present invention relates generally to polycystic ovary syndrome (PCOS) and more specifically to compositions and methods for detection and diagnosis of PCOS.

BACKGROUND OF THE INVENTION

PCOS is the most common endocrine disturbance of women of reproductive age, affecting approximately 6-10% of women in this population, and is a common cause of infertility. PCOS has a similar incidence among ethnic and racial groups.

PCOS is characterized by traits that include but are not necessarily limited to abnormal acxumulation of small follicles within the ovary, oligomenonrrhea or amenorrhea, acne, *Acanthosis nigricans*, male pattern alopecia, increased ovarian androgen production, infertility/first trimester miscarriage, hirsutism, hyperinsulinemia/insulin resistance and obesity. Clinical criteria for PCOS include hyperandrogenemia, increased total testosterone and/or bioavailable testosterone, oligo-ovulation, polycystic ovaries and fewer than six periods/year. When attempting to definitively diagnose PCOS, other causes of these symptoms (e.g., tumors secreting androgens, congenital adrenal hyperplasia, Cushing's syndrome) need to be excluded.

Currently, diagnosis of PCOS is complex and frequently involves testing of hormone levels to rule out late-onset congenital adrenal hyperplasia (LOCAH) or non-classical adrenal hyperplasia (NCAH), and Cushing's syndrome. Testing frequently performed includes measurements of Testosterone, Dehydroepiandrosterone sulfate (DHEAS), 17α-Hydroxyprogesterone, Sex hormone-binding globulin (SHBG), prolactin levels, thyroid function tests, and transvaginal ultrasound to assess ovarian morphology. Thus, there remains a longstanding need for improved compositions and methods that can be used in connection with PCOS diagnosis, for monitoring therapeutic/surgical interventions, and for selecting patients for personalized therapeutic approaches. The present invention meets these and other needs.

SUMMARY OF THE INVENTION

The present invention provides compositions and methods for making or for aiding in making a diagnosis of PCOS. In general, the method comprises detection and/or quantitation of DENND1A Variant 2 mRNA or DENND1A Variant 2 protein in a sample obtained or derived from a subject.

The invention is suitable for testing samples from any human individual, including females and males of any age, regardless of medical condition. Thus, in various embodiments, the invention provides a method that can be used for convenient and rapid determination of the presence and/or amount of DENND1A Variant 2 mRNA and/or protein in a wide variety of biological samples, non-limiting examples of which are described further below. The invention is expected to provide earlier, easier and more definitive diagnosis of PCOS than what has heretofore been available. In certain embodiments, the invention permits testing of any biological sample, including but not limited to any tissue or biological fluids, non-limiting examples of which include blood, urine, plasma, serum, or mucosal fluid, including saliva. The invention includes testing of samples which contain exosomes, such as a sample of blood, urine, or saliva which contains or would be expected to contain exosomes. In certain embodiments, the invention is performed on a sample that is non-invasively obtained from the subject.

Detection of the DENND1A Variant 2 mRNA and/or protein can be performed using any method. In various embodiments, the mRNA is detected using a polymerase chain reaction (PCR)-based approach, such as real time (RT)-PCR. In alternative approaches, DENND1A Variant 2 mRNA is detected by hybridization of a labeled probe, whereby the hybridized labeled probe is detected. As such, the method is amenable to being performed as part of a multiplexed assay, such as on a chip or an array. In alternative embodiments, the DENND1A Variant 2 protein is detected. Detection/quantitation of the DENND1A Variant 2 protein can be performed using, for example, any immunological-based detection mechanism. In various approaches, detecting the DENND1A Variant 2 protein is performed using either polyclonal or monoclonal antibodies so that a complex comprising DENND1A Variant 2 protein and the antibodies is detected.

In another aspect, the invention provides a method for selecting an individual as a candidate for therapy for PCOS. This involves testing a sample from an individual for DENND1A Variant 2 mRNA and/or DENND1A Variant 2 protein, and subsequent to detecting/quantitating the DENND1A Variant 2 mRNA or protein in the sample, designating the individual as a candidate for the PCOS therapy (or not so designating, if the sample does not contain DENND1A Variant 2 mRNA or protein, or contains less of either as compared to a reference). In certain embodiments, the method involves treating the individual for PCOS subsequent to detecting/quantitating the DENND1A Variant 2 mRNA or protein in a sample from the individual.

The invention also provides a product for use in making or aiding diagnosis of PCOS. The product can comprise reagents, such as probes and/or primers, wherein at least one of the probes and/or the primers can specifically hybridize to DENND1A Variant 2 mRNA. The product can additionally contain packaging, and printed material indicating that the product is to be used to detect DENND1A Variant 2 mRNA as an indicator of PCOS. The printed material can include instructions as to how the reagents provided as part of the product are to be used to make or aid a PCOS diagnosis.

BRIEF DESCRIPTION OF THE FIGURES

FIG. 1A shows that CYP17 mRNA accumulation was significantly increased in PCOS theca cells as compared to normal theca cells treated under basal and forskolin stimulated conditions (*, P<0.05). FIG. 1B shows that DHEA biosynthesis in PCOS theca cells was significantly increased under both basal and forskolin stimulated conditions (*, P<0.05).

FIG. 3A shows that DENND1A Variant 1 is not differentially expressed in normal and PCOS theca cells. In contrast, DENND1A Variant 2 mRNA accumulation was significantly increased under both basal (*, P<0.01) and forskolin (, P<0.05) stimulated conditions in PCOS theca cells, as compared to normal cells.

FIGS. 5A and 5B provide a photographic representation of Western Blot analysis demonstrating that DENND1A Variant 2 protein expression is increased in PCOS theca cells. FIG. 5A depicts a representative Western Blot analysis which shows increased 62 kD DENND1A Variant 2 (DENND1A.V2) in PCOS theca cells. FIG. 5B shows that the 62 kD DENND1A Variant 2 was present in the nuclear component of PCOS theca cells, but the 110 kD DENND1A Variant 1 was not detected in normal or PCOS whole cell or nuclear extracts. These data demonstrate that DENND1A Variant 2 protein is present in the nucleus, and may traffic from the cell membrane where DENND1A proteins are thought to associate with clathrin to the nucleus to regulate a variety of cell functions in the ovarian theca cell.

FIGS. 6A, 6B, 6C and 6D provide graphical representations of data demonstrating that expression of DENND1A Variant 2 in normal theca cells results in elevated androgen production, augmented CYP17 mRNA accumulation, and increased CYP17A1 promoter regulation. FIG. 6A shows that all doses of DENND1A.V2 adenovirus significantly increased forskolin-stimulated DHEA production compared with control Null (empty) adenovirus (*, P<0.05). FIG. 6B shows that infection of normal theca cells with 3.0 pfu of adenovirus expressing DENND1A.V2 results in a significant increase in forskolin-stimulated DHEA biosynthesis compared to empty virus infected cells (*, P<0.05). FIG. 6C shows that both 1.0 and 10 pfu DENND1A.V2 adenovirus significantly increased CYP17 mRNA accumulation in normal cells, with and without forskolin stimulation, as compared to infection with Null adenovirus (*, P<0.05). FIG. 6D shows that DENND1A.V2 adenovirus increases both basal (*, P<0.05), and forskolin-stimulated (**, P<0.01). −770 CYP17A1 promoter activity as compared to Null adenovirus.

As shown in FIG. 7A, DENND1A.V2 shRNA1 and shRNA2 retrovirus plasmid significantly inhibited both basal (*, P<0.05) and forskolin (*, P<0.01) stimulated CYP17 mRNA accumulation in PCOS theca cells. As shown in FIG. 7B, co-transfection of −235/+44 of the CYP17A1 promoter fused to the luciferase gene in a pGL3 plasmid with DENND1A.V2 shRNA1 and shRNA2 resulted in a significant inhibition of forkolin-dependent CYP17A1 reporter activity in PCOS theca cells, compared to Scrambled shRNA (*, P<0.05). To evaluate the effect of knockdown of DENND1A.V2 on DHELA biosynthesis, PCOS theca cells were infected with a silencing shRNA DENND1A.V2 lentivirus or a control non-silencing lentivirus in the presence or absence of forskolin for 72 h. As shown in FIG. 7C, infection with silencing shRNA DENND1A.V2 lentivirus significantly inhibited forskolin-stimulated DHEA biosynthesis (*, P<0.05).

As shown in FIG. 8A, DENND1A.V2 significantly increased both basal and LH/hCG-stimulated DHEA biosynthesis (*, P<0.05). As shown in FIG. 8B, DENND1A.V2 significantly increased LH/hCG-stimulated CYP17A1 promoter function (*, P<0.05).

DETAILED DESCRIPTION OF THE INVENTION

Figure 1A:
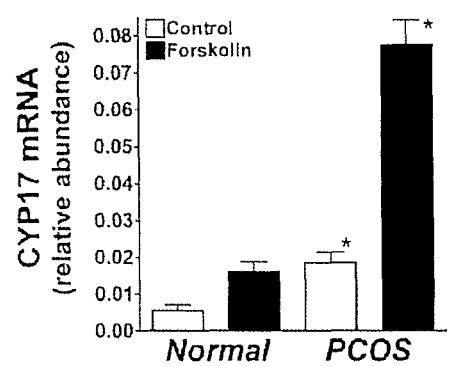
FIGS. 1A and 1B provide graphical summaries of data which together demonstrate that both basal and cAMP-stimulated CYP17 mRNA accumulation and DHEA production are increased in PCOS theca cells propagated in long-term culture.

The present invention provides compositions and methods that are useful for, among other purposes, diagnosis of PCOS or any other condition that is positively correlated with expression of the DENND1A Variant 2 mRNA and/or protein, as further described herein. The invention is also suitable for determining whether or not an individual is a candidate for PCOS therapy, for development of a treatment regime for an individual who is diagnosed with PCOS, and for monitoring PCOS therapy.

The method generally comprises testing a sample for the presence or absence of DENND1A Variant 2 mRNA or protein, or for comparing an amount of DENND1A Variant 2 mRNA or protein to a reference. In embodiments of the invention, determining the presence of DENND1A Variant 2 mRNA or protein aids in the diagnoses of a condition that is positively correlated with DENND1A Variant 2 expression. In one embodiment, determining the presence of DENND1A Variant 2 mRNA or protein is considered a diagnosis of PCOS.

The DENND1A Variant 1 and DENND1A Variant 2 are also referred to as the "DENND1A isoform 1" and "DENND1A isoform 2" respectively, and as "DENND1A.V1" and "DENND1A.V2", respectively.

The DENND1A Variant 2 cDNA sequence is: (SEQ ID NO: 1):

(SEQ ID NO: 1)

```
0001    cgcgcgccgg gcacgcgcgc cggcgaccat ggcgttcgcc gggctggagc gagtacatta
0061    accccctggag gcggcggcgg cggcgaggga gcgagcctcg agcgggcggg ccccagcctg
0121    agggaaggga ggaaggggcg gggagagcgc cagagggagg ccggtcggcc gcgggcgggc
0181    gggcagcgca cgccgagcg gggcccgcgg gcccatgagg aggcctgggg accatgggct
0241    ccaggatcaa gcagaatcca gagaccacat ttgaagtata tgttgaagtg cctatcccca
0301    ggacaggtgg cactctttca gatcctgagg tgcagaggca attcccggag gactacagtg
0361    accaggaagt tctacagact ttgaccaagt tttgtttccc cttctatgtg gacagcctca
0421    cagttagcca agttggccag aacttcacat tcgtgctcac tgacattgac agcaaacaga
0481    gattcgggtt ctgccgctta tcttcaggag cgaagagctg cttctgtatc ttaagctatc
0541    tcccctggtt cgaggtattt tataagctgc ttaacatcct ggcagattac acgacaaaaa
0501    gacaggaaaa tcagtggaat gagcttcttg aaactctgca caaacttccc atccctgacc
0661    caggagtgtc tgtccatctc agcgtgcatt cttattttac tgtgcctgat accagagaac
0721    ttcccagcat acctgagaat agaaatctga cagaatattt tgtggctgtg gatgttaaca
0781    acatgttgca tctgtacgcc agtatgctgt acgaacgccg gatactcatc atttgcagca
0841    aactcagcac tctgactgcc tgcatccacg ggtctgcggc gatgctctac cccatgtact
0901    ggcagcacgt gtacatcccc gtgctgccgc cgcatctgct ggactactgc tgtgctccca
0961    tgccctacct cataggaatc catttaagtt taatggagaa agtcagaaac atggccctgg
1021    atgatgtcgt gatcctgaat gtggacacca cacccctgga aacccccttc gatgacctcc
1081    agagcctccc aaacgacgtg atctcttccc tgaagaacag gctgaaaaag gtctccacaa
1141    ccactgggga tggtgtggcc agagcgttcc tcaaggccca ggctgctttc ttcggtagct
1201    accgaaacgc tctgaaaatc gagccggagg agccgatcac tttctgtgag gaagccttcg
1261    tgtcccacta ccgctccgga gccatgaggc agttcctgca gaaccccaca cagctgcagc
1321    tcttcaagca gtttattgat ggtcgattag atcttctcaa ttccggcgaa ggtttcagtg
1381    atgttttga agaggaaatc aacatgggcg agtacgctgg cagtgacaaa ctgtaccatc
1441    agtggctctc cactgtccgg aaaggaagtg gagcaattct gaatactgta agaccaaag
1501    caaatccggc catgaagact gtctacaagt cgcaaaaga tcatgcaaaa atgggaataa
1561    aagaggtgaa aaaccgcttg aagcaaaagg acattgccga aatggctgc gcccccaccc
1621    cagaagagca gctgccaaag actgcaccgt ccccactggt ggaggccaag gaccccaagc
1681    tccgagaaga ccggcggcca atcacagtcc actttggaca ggtgcgccca cctcgtccac
1741    atgttgttaa gagaccaaag agcaacatcg cagtggaagg ccggaggacg tctgtgccga
1801    gccctgagca aaacaccatt gcaacaccag ctacactcca catcctacag aaaagcatta
1861    cccattttgc ggccaagttc ccgacgagag ctggacctc ttcatcacat tgacttacgc
1921    cgttactttt ccagactggg cagagggct gacttcgcag tgtgtgccaa agagccggtg
1981    tctgataatc ccattttcct gcttatcacc tgaactgtgt cagtatcact tttagttttg
2041    ttggttggtt ggtttgttat tgtttaata tgccctgttt tctacttctg ttggaaaata
2101    tttggggttg aaataaacca gtgggagcat ggaaaaaaaa aaaaaaaaa aaaaaaaaa
2161    aaaaaa
```

The DENND1A Variant 2 amino acid sequence is (SEQ ID NO: 2):

(SEQ ID NO: 2)

MGSRIKQNPETTFEVYVEVAYPRTGGILSDPEVQRQFPEDYSDQEVLQTLTKFCFPFYVDSLTVSQVGQNFTFVL

TDIDSKQRFGFCRLSSGAKSCFCILSYLPWFEVFYKLLNILADYTTKRQENQWNELLETLHKLPIPDPGVSVHLS

-continued

VHSYFTVPDTRELPSIPENRNLTEYFVAVDVNNMLHLYASMLYERRILIICSKLSTLTACIHGSAAMLYPMYWQH
VYIPVLPPHLLDYCCAPMPYLIGIHLSLMEKVRNMALDDVVILNVDTNTLETPFDDLQSLPNDVISSLKNRLKKV
STTTGDGVARAFLKAQAAFFGSYRNALKIEPEEPITFCEEAFVSHYRSGAMRQFLQNATQLQLFKQFIDGRLDLL
NSGEGFSDVFEEEINMGEYAGSDKLYHQWLSTVRKGSGAILNTVKTKANPAMKTVYKFAKDHAKMGIKEVKNRLK
QKDIAENGCAPTPEEQLPKTAPSPLVEAKDPKLREDRRPITVHFGQVRPPRPHVVKRPKSNIAVEGRRTSVPSPE
QNTIATPATLHILQKSITHFAAKFPTRGWTSSSH

The DENND1A Variant 1 cDNA sequence is (SEQ ID NO: 3):

(SEQ ID NO: 3)
```
0001    cgcgcgccgg gcacgcgcgc cggcgaccat ggcgttcgcc gggctggagc gagtacatta
0061    accccctggag gcggcggcgg cggcgaggga gcgagcctcg agcgggcggg ccccagcctg
0121    agggaaggga ggaaggggcg gggagagcgc cagagggagg ccggtcggcc gcgggcgggc
0181    gggcagcgca gcgccgagcg gggcccgcgg gcccatgagg aggcctgggg accatgggct
0241    ccaggatcaa gcagaatcca gagaccacat ttgaagtata tgttgaagtg cctatcccca
0301    ggacaggtgg cactctttca gatcctgagg tgcagaggca attcccggag gactacagtg
0361    accaggaagt tctacagact ttgaccaagt tttgtttccc cttctatgtg acagcctcaa
0421    cagttagcca agttggccag aacttcacat tcgtgctcac tgacattgac agcaaacaga
0481    gattcgggtt ctgccgctta tcttcaggag cgaagagctg cttctgtatc ttaagctatc
0541    tcccctggtt cgaggtattt tataagctgc ttaacatcct ggcagattac acgacaaaaa
0601    gacaggaaaa tcagtggaat gagcttcttg aaactctgca caaacttccc atccctgacc
0661    caggagtgtc tgtccatctc agcgtgcatt cttattttac tgtgcctgat accagagaac
0721    ttcccagcat acctgagaat agaaatctga cagaatattt tgtggctgtg gatgttaaca
0781    acatgttgca tctgtacgcc agtatgctgt acgaacgccg gatactcatc atttgcagca
0841    aactcagcac tctgactgcc tgcatccacg gtctgcggc gatgctctac cccatgtact
0901    ggcagcacgt gtacatcccc gtgctgccgc cgcatctgct ggactactgc tgtgctccca
0961    tgccctacct cataggaatc catttaagtt taatggagaa agtcagaaac atggccctgg
1021    atgatgtcgt gatcctgaat gtggacacca caccctgga aaccccctcc gatgacctcc
1081    agagcctccc aaacgacgtg atctcttccc tgaagaacag gctgaaaaag gtctccacaa
1141    ccactgggga tggtgtggcc agagcgttcc tcaaggccca ggctgctttc ttcggtagct
1201    accgaaacgc tctgaaaatc gagccggagg agccgatcac tttctgtgag gaagccttcg
1261    tgtcccacta ccgctccgga gccatgaggc agttcctgca gaacgccaca cagctgcagc
1321    tcttcaagca gtttattgat ggtcgattag atcttctcaa ttccggcgaa ggtttcagtg
1381    atgtttttga agaggaaatc aacatgggcg agtacgctgg cagtgacaaa ctgtaccatc
1441    agtggctctc cactgtccgg aaaggaagtg gagcaattct gaatactgta aagaccaaag
1501    caaatccggc catgaagact gtctacaagt tcgcaaaaga tcatgcaaaa atgggaataa
1561    aagaggtgaa aaaccgcttg aagcaaaagg acattgccga aatggctgc gccccaccc
1621    cagaagagca gctaccaaag actgcaccgt ccccactggt ggaggccaag gaccccaagc
1681    tccgagaaga ccggcggcca atcacagtcc actttggaca ggtgcgccca cctcgtccac
1741    atgttgttaa agaccaaag agcaacatcg cagtggaagg ccggaggacg tctgtgccga
1801    gccctgagca gccgcagccg tatcggacac tcagggagtc agacagcgcg aaggcgacg
1861    aggcagagag tccagagcag caagtgcgga agtccacagg ccctgtccca gctccccctg
1921    accgggctgc cagcatcgac cttctggaag acgtcttcag caacctggac atggaggccg
```

-continued

```
1981  cactgcagcc actgggccag gccaagagct tagaggacct tcgtgccccc aaagacctga
2041  gggagcagcc agggaccttt gactatcaga ggctggatct gggcgggagt gagaggagcc
2101  gcggggtgac agtggccttg aagcttaccc acccgtacaa caagctctgg agcctgggcc
2161  aggacgacat ggccatcccc agcaagcccc cagctgcctc ccctgagaag ccctcggccc
2221  tgctcgggaa ctccctggcc ctgcctcgaa ggccccagaa ccgggacagc atcctgaacc
2281  ccagtgacaa ggaggaggtg cccacccta ctctgggcag catcaccatc cccccggccc
2341  aaggcaggaa gacccagag ctgggcatcg tgcctccacc gcccattccc cgcccggcca
2401  agctccaggc tgccggcacc gcacttggtg acgtctcaga gcggctgcag acggatcggg
2461  acaggcgagc tgccctgagt ccagggctcc tgcctggtgt tgtccccaa ggccccactg
2521  aactgctcca gccgctcagc cctggcccg gggctgcagg cacgagcagt gacgccctgc
2581  tcgccctcct ggacccgctc agcacagcct ggtcaggcag caccctcccg tcacgcccg
2641  ccaccccgaa tgtagccacc ccattcaccc cccaattcaa cttccccct gcagggacac
2701  ccacccatt cccacagcca ccactcaacc cctttgtccc atccatgcca gcagccccac
2761  ccaccctgcc cctggtctcc acaccagccg ggcctttcgg ggcccctcca gcttccctgg
2821  ggccggcttt tgcgtccggc ctcctgctgt ccagtgctgg cttctgtgcc cctcacaggt
2881  ctcagcccaa cctctccgcc ctctccatgc caacctctt tggccagatg cccatgggca
2941  cccacacgag cccctacag ccgctgggtc ccccagcagt tgcccgtcg aggatccgaa
3001  cgttgcccct ggcccgctca agtgccaggg ctgctgagac caagcagggg ctggccctga
3061  ggcctggaga cccccgctt ctgcctccca ggccccctca aggcctggag ccaacactgc
3121  agccctctgc tcctcaacag gccagagacc cctttgagga tttgttacag aaaaccaagc
3181  aagacgtgag cccgagtccg gccctggccc cggccccaga ctcggtggag cagctcagga
3241  agcagtggga gaccttcgag tgagccgggc cctgagggtg ggggatgcac cgaggcccga
3301  gggtccgtcc actgctgcag ttccgaggct cccccgccac tctctctctg cccaggttct
3361  gctggtggga agagatggga ccctctctg ctgcccctc ctcccctcca cactgcccat
3421  ctctgatgtc tggccctggg gaatggcacc agttccagcc tgggaatcaa cccagttcct
3481  gagtgcccat cccacccgc ggttgcctct cctcggcacc cttgattggg ttttgcacta
3541  aagaggtcag ctgggccaat gatattgctc cagaccgagt cctacccacc ttccccggga
3601  agtgtcccaa gaggctccga aggcctcccc tccgagccca gctctcctgt ctcctccaca
3661  gccaggccct gcacgcccac ctcctcggac acaggtgaca gggttaccct ccagtttgag
3721  ctcatctgca cgagacacag gtagcttggg gttgaagtta ggactcctcc tgggctggag
3781  gatttacctg gtggggcact tccagactgt ttctagcaat atacacacac gttctttcct
3841  gtgtcttcac cccaaaactt cagttgattc tgacctggga ggatctgggg accaggggt
3901  cttgagctgc cttgtgatac acagccccag ccaccctgca cggggctgc gagcaccagc
3961  aactttgatt tatagaagga aaatggaaac cccatctga gtattttggg aggagccccc
4021  agccctcatc cagctctgga acgctgatac ctccaggtac tccctcact gtcaaagctg
4081  gggctcagcc tcttgtcatc tggagctttg tgggcaaagc tgagaagctg caacccagat
4141  ttcaacccaa aaaggtcaag ctgaatgcct cagactgatg tggaaggcag ctggccttcc
4201  tgggttggaa cgaggcagtg gccctgagcc cttctccag ggccaggtag aaaggacaaa
4261  cttggtctct gcctcgggga agcaggagga gggctagaag ccagtccctc cccacctgcc
4321  cagagctcca ggccagcaca gaaattcctg aggccaacgt caccaaagtt agattgaatg
4381  tttattatct ttcttttttcc tttttacctt attgatttga tgaatcttga aatggattca
```

```
4441        tttccataaa ccaagttaaa gtatggcccg accatttaag aaaacaacca tctgagacac 4501        gcaggaaatt gtgagcattt cgacccgagc tctcatttcc tatttgtgaa gggtcagaca 4561        cagtctaccc aggagtgtct gggggacaag ggggtctctg gagatgtcac ccagggagcc 4621        ccctctatgt crgagaggct gccactgctg cacatgctca gtgaggcttg gcggccatcc 4681        tggcacatgg ctcttcctgg gtcaaccgtg acctgtctgg ctcaggaatg ggctctggct 4741        gctgggggag ccgtgtcact cctgggccat gggggcacct cctgggcact taggtgtttc 4801        agcatagatt ccagtttcgc accctgagca gaccccagg ccccatccgg gatagggcag 4861        aggaggtgct ggcggcccca ggaaggagg gtgtgtaccc caaggccccc tggctgtgct 4921        gaggggctgg ggtgagcgct ccatgttcac atgagcactg ctgcctcttc acttgtggga 4981        cttttgcaa acccaaggat gaactttgtg tgcattcaat aaaatcatct tggggaagag 5041        g
```

The DENND1A Variant 1 amino acid sequence is (SEQ ID NO: 4):

(SEQ ID NO: 4)

MGSRIKQNPETTFEVYVEVAYPRTGGTLSDPEVQRQFPEDYSDQEVLQTLTKFCFPPFYVDSLTVSQVGQNFTFVL

TDIDSKQRFGFCRLSSGAKSCFCILSYLPWFEVFYKLLNILADYTTKRQENQWNELLETLHKLPIPDPGVSVHLS

VHSYFTVPDTRELPSIPENRNLTEYFVAVDVHNMLHLYASMLYERRILIICSKLSTLTACIHGSAAMLYPMYWQH

VYIPVLPPHLLDYCCAPMPYLIGIHLSLMEKVRNMALDDVVILNVDTNTLETPFDDLQSLPNDVISSLKNRLKKV

STTTGDGVARAFLKAQAAFFGSYRNALKIEPEEPITFCEEAFVSHYRSGAMRQFLQNATQLQLFKQFIDGRLDLL

NSGEGFSDVFEEEINMGEYAGSDKLYHQWLSTVRKGSGAILNTVKTKANPAMKTVYKFAKDHAKMGIKEVKNRLK

QKDIAENGCAPTPEEQLPKTAPSPLVEAKDPKLREDRRPITVHFGQVRPPRPHVVKRPKSNIAVEGRRTSVPSPE

QPQPYRTLRESDSAEGDEAESPEQQVRKSTGPVPAPPDRAASIDLLEDVFSNLDMEAALQPLGQAKSLEDLRAPK

DLREQPGTFDYQRLDLGGSERSRGVTVALKLTHPYNKLWSLGQDDMAIPSKPPAASPEKPSALLGNSLALPRRPQ

NRDSILNPSDKEEVPTPTLGSITIPRPQGRKTPELGIVPPPPIPRPAKLQAAGAALGDVSERLQTDRDRRAALSP

GLLPGVVPQGPTELLQPLSPGPGAAGTSSDALLALLDPLSTAWSGSTLPSRPATPNVATPFTPQFSFPPAGTPTP

FPQPPLNPFVPSMPAAPPTLPLVSTPAGPFGAPPASLGPAFASGLLLSSAGFCAPHRSQPNLSALSMPNLFGQMP

MGTHTSPLQPLGPPAVAPSRIRTLPLARSSARAAETKQGLALRPGDPPLLPPRPPQGLEPTLQPSAPQQARDPFE

DLLQKTKQDVSPSPALAPAPDSVEQLRKQWETFE

For each cDNA sequence presented herein, the invention includes the mRNA equivalent of the cDNA, meaning that the invention includes each cDNA sequence wherein each T is replaced by U. In embodiments, determining polynucleotides comprising or consisting of the cDNA sequence or segments thereof is considered to be the same as determining the corresponding mRNA.

Our experiments indicate that DENND1A.V2 is central to the pathogenesis of PCOS because of its role in controlling cell signaling, making it a strong biomarker of the disease. The present invention includes but is not limited to the novel finding that DENND1A Variant 2 mRNA and protein is increased in PCOS ovarian theca cells, as well as in other tissues, including but not necessarily limited to urine exosomes. Accordingly, it is demonstrated herein that increased DENND1A Variant 2 is a characteristic of PCOS and can be used as a diagnostic marker for PCOS. In furtherance of determining the relationship between DENND1A Variant 2 and PCOS, we present data that show that the presence of DENND1A Variant 2 results in an increase in ovarian androgen production, as well as increased CYP17A1 gene expression, the latter due to increased transcription driven from the CYP17A promoter. We also demonstrate that transfection of ovarian theca cells with DENND1A Variant 2 results in decreased LKB1 and ERK phosphorylation, which are associated with conversion of normal cells to a PCOS phenotype. Thus, it is likely that DENND1A Variant 2 acts as an upstream signaling component which can affect down-stream signaling events, including but not necessarily limited to acting on Mitogen-activated protein kinase (MAPK) and LKB1/5' adenosine monophosphate-activated protein kinase (AMPK) signaling pathways. It is believed this results in increased androgen production consistent with that observed in PCOS. Data presented herein also demonstrate that targeted blockage of DENND1A Variant 2 by RNAi-mediated mRNA degradation can inhibit the deleterious effects of DENND1A Variant 2, at least in respect of its effect on CYP17A1 expression, thereby further confirming its role as a diagnostic marker, and that it likely plays a material role in the etiology of PCOS. These results also implicate DENND1A Variant 2 as a target for therapeutic intervention.

While the present invention is amenable to testing a wide variety of biological samples, we notably demonstrate that DENND1A Variant 2 mRNA can be detected in urine exosomal RNA, and thus can be expected to be detectable in any other biological sample, including but not limited to biological fluids. Accordingly, in certain embodiments, the invention provides a non-invasive approach for detecting DENND1A Variant 2 in samples obtained from any human subject. Thus, the invention permits testing from any individual, regardless of age, gender, overall health or disease condition. This is a particular concern when considering the diagnosis in adolescents or pubertal children where non-invasive testing would provide great value. The invention thus includes in various aspects tools for use in a convenient and rapid approach for determining the presence and/or amount of DENND1A Variant 2 in a wide variety of biological samples, illustrative embodiments of which are described further below. These tools are expected to facilitate earlier, easier and more definitive diagnosis of PCOS than previously available approaches.

The biological sample tested according to the invention can be any biological sample that contains or would be suspected to contain nucleic acids and/or protein. The sample can be a tissue sample, or a sample of a biological liquid. Non-limiting examples of tissues include samples obtained by way of biopsy, such as a biopsy of ovarian tissue, or a sample of mucosa. The sample can be a sample comprising theca cells. In other non-limiting examples, the sample can be a liquid sample such as blood, urine, plasma, serum, or mucosal fluid, including saliva. In certain embodiments, the sample comprises exosomes, such as a sample of blood or urine which contains or would be expected to contain exosomes. In other embodiments, the sample can be a sample of reproductive tissue, or exudate such as ovarian exudate or endometrial tissue or exudate. In a preferred embodiment, the sample is one that is non-invasively obtained from the subject, such as a sample comprising urine, a mucosal sample, or a sample of oral fluid, such as saliva or sputum.

In certain approaches, the sample is obtained from the subject and used directly in determining the presence or absence or amount of the DENND1A Variant 2. In other embodiments, the biological sample is obtained and subjected to a processing step before the biological sample is used in testing for the DENND1A Variant 2. In some examples, the processing step can be carried out to isolate, and/or purify and/or amplify the DENND1A Variant 2 mRNA, or to isolate and/or purify the DENND1A Variant 2 protein.

In certain embodiments, the invention is useful for testing a sample from an pre-pubescent or adolescent human female. In certain examples, the female can be as young as eight years old. In certain embodiments the sample is from a human female that is younger that eight years old, such as an infant. In other embodiments, the invention is useful for testing a sample obtained from a human male. In this regard, it is expected that determining DENND1A Variant 2 mRNA or protein in a sample obtained from a human male will be useful because we suspect there is involvement of DENND1A Variant 2 in certain conditions in human males, such as metabolic disorders that comprise conditions affecting lipid metabolism, including but not limited to hyperlipidemias and cardiovascular conditions related to lipid metabolism. In one embodiment, the subject tested according to the invention is a human male who has a female sibling who has been diagnosed with PCOS.

Suitable techniques for determining the presence or absence or quantitating DENND1A Variant 2 mRNA include but are not limited to hybridization of probes or primers directed to DENND1A Variant 2 mRNA, or by using various chip technologies, polynucleotide or oligonucleotide arrays, and combinations thereof. Thus, in various embodiments, probes to the DENND1A Variant 2 mRNA or a DNA equivalent of it can be arranged and/or fixed on a solid support.

DENND1A Variant 2 mRNA may be tested directly or may be amplified enzymatically in vitro by, for example, use of the polymerase chain reaction (PCR), Real-Time (RT) PCR, including quantitative real-time (QT-RT) PCR analysis, or any other in vitro amplification methods. For amplification reactions, primers can be designed which hybridize to DENND1A Variant 2 mRNA, and used to obtain nucleic acid amplification products (i.e., amplicons). Those skilled in the art will recognize how to design suitable primers and perform amplification and/or hybridization reactions in order to carry out various embodiments of the method of the invention. In general, the primers should be long enough to be useful in amplification reactions, and generally primers which are at least 12 bases in length are considered suitable for such purposes, but primers as short as 8 bases can be used depending on reaction conditions. The primers/probes used for detecting DENND1A Variant 2 RNA can comprise modifications, such as being conjugated to one or more detectable labels, such as fluorophores in the form of a reporter dye and/or a quenching moiety for use in reactions such as real time (RT)-PCR, which allow quantitation of DNA amplified from RNA, wherein the quantitation can be performed over time concurrent with the amplification. In one embodiment, the amplification reaction comprises at least one polynucleotide probe specific for DENND1A Variant 2 mRNA, wherein the probe includes one terminal nucleotide modified to include a fluorescent tag, and the other terminal nucleotide modified to comprise a moiety that quenches fluorescence from the fluorescent tag. For instance, for use in RT-PCR, such a probe can be designed so that it hinds with specificity to a portion of DENNDA1 Variant 2 or its complement that is between and does not overlap sequences to which two RT-PCR primers hybridize. Using this design, signal from the fluorescent tag will be quenched until the probe is degraded via exonuclease activity of the polymerase during amplification, at which point the fluorescent nucleotide will be separated from the quenching moiety and its signal will be detectable.

It will be recognized by those skilled in the art that while particular sequences of primers are provided herein, other primer sequences can be designed to detect the DENND1A Variant 2 mRNA. In certain embodiments, at least two synthetic oligonuclcotide primers are used in an amplification reaction. The primers in different embodiments can be from 8 to 100 nucleotides in length, inclusive, and including all integers there between. The primers are of sufficient length and nucleotide composition to specifically hybridize under stringent conditions to DENND1A Variant 2 mRNA, and to cDNA equivalents thereof. In non-limiting examples, a first synthetic primer for use in an amplification reaction comprises or consists of a polynucleotide sequence that is identical to at least 8 contiguous nucleotides in the Variant 2 mRNA sequence, and a second primer comprises or consists of a polynucleotide sequence that is complementary to at least 8 contiguous nucleotides in the Variant 2 mRNA sequence. Longer primers can tolerate a certain number of mismatched nucleotides that will be apparent to one skilled in the art, and are dictated by such well known parameters as melting temperature and stringency. The primers can be designed such that they do not have complementarity to one another. In one embodiment, the primers are designed to amplify the following segment of the Variant 2 mRNA sequence, which comprises a 3'-mRNA sequence of DENND1A Variant 2 that is different than the DENND1A mRNA Variant 1 sequence. This distinct 3' segment includes a stop codon and a frameshift resulting in a shorter mRNA and distinct carboxy-terminal 33 amino acid sequence in DENND1A Variant 2. The message comprises a stop codon ending at nt1913 and an untranslated sequence beginning at nt1914. The mRNA of DENDA1A Variant two has mRNA coding sequence that is distinct from DENND1A Variant 1 from 1811-1913. The sequence of the 3'-region shown is the cDNA equivalent of the DENND1A Variant 2 mRNA segment, as indicated by the nucleotide positions:

between. In certain embodiments, such probe or primer is identical or complementary to only the portion of DENND1A Variant 2 mRNA consisting of SEQ ID NO:6.

The invention accordingly provides primers which can amplify a polynucleotide comprising or consisting of SEQ ID NO:5 or SEQ ID NO:6.

In non-limiting embodiments, the primers that are used to detect and/or quantitate DENND1A Variant 2 mRNA are as follows: Forward Primer (5'-GGGCFGACTTCGCAGTGTGT-3' SEQ ID NO:7), Reverse Primer (5-ACAGTTCAGGTGATAAGCAG-GAAA-3' SEQ ID) NO:8).

```
                                                        (SEQ ID NO: 5)
1811           aaacaccatt gcaacaccag ctacactcca catcctacag aaaagcatta 1861    cccatttgc ggccaagttc ccgacgagag gctggacctc ttcatcacat tgacttacgc 1921    cgttactttt ccagactggg caaaggggct gacttcgcag tgtgtgccaa agagccggtg 1981    tctgataatc ccattttcct gcttatcacc tgaactgtgt cagtatcact tttagttttg 2041    ttggttggtt ggtttgttgt ttgtttaata tgccctgttt tctacttctg ttggaaaata 2101    tttggggttg aaataaacca gtgggagcat ggaaaaaaaa aaaaaaaaa aaaaaaaaaa 2161    aaaaaa
```

In non-limiting examples, the method involves detecting and/or quantitating DENND1A Variant 2 mRNA by amplifying a segment of the mRNA, wherein the amplification products comprise SEQ ID NO:5, or a contiguous shorter segment thereof, wherein the continuous segment can exclude, for example, the poly-A tail. Thus, in one embodiment, the amplification product can comprise the distinct DENNDA1 Variant 2 (mRNA or cDNA) 3' open frame between and including nucleotide 1811-1913 and 3' UTR sequence from 1914-2132:

In one embodiment, DENND1A Variant 2 mRNA can be measured via hybridization of a detectably labeled probe, and detecting the signal from the detectable label if the probe is hybridized to the mRNA, or its cDNA equivalent. The detectably labeled probe can be of the same length and nucleotide composition as described above for primers, or it can be longer. One non-limiting example of a probe that can be used in detecting/quantitating DENND1A Variant 2 mRNA has the sequence: CCAAAGAGC/ZEN/CGG TGT CTGATAATCCCA, (SEQ ID NO:9) wherein "ZEN" signi-

```
                                                        (SEQ ID NO: 6)
1811           aaacaccatt gcaacaccag ctacactcca catcctacag aaaagcatta 1861    cccatttgc ggccaagttc ccgacgagag gctggacctc ttcatcacat tgacttacgc 1921    cgttgctttt ccagactggg cagaggggct gacttcgcag tgtgtgccaa agacccggtg 1981    tctgataatc ccattttcct gcttatcacc tgaactgtgt cagtatcact tttagttttg 2041    ttggttggtt ggtttgttgt ttgtttaata tgccctgttt tctacttctg ttggaaaata 2101    tttggggttg aaataaacca gtgggagcat gg
``` or a segment of SEQ ID NO:6 that is, for example, at least 10 nucleotides in length. The nucleotide numbering in this sequence is maintained from the full length cDNA sequence presented above. In one embodiment, the amplification products comprises a product that comprises at least 18 contiguous nucleotides of SEQ ID NO:6. In one embodiment, at least 18 contiguous polynuclcotides are present in an amplification product that is from 24 to 200 base pairs (hp), inclusive and including all integers there between. In one embodiment, such an amplification product is from 80-100 bp. Those skilled in the at will recognize given the benefit of the present disclosure that a probe and/or primer for use in the invention can be complimentary or identical to a contiguous segment of SEQ ID NO:6. In one embodiment, such probe or primer is at least 18 nucleotides in length. In one embodiment, such probe or primer is from 18 to 24 nucleotides in length, inclusive, and including all digits there fies location of a secondary quenching moiety which increases sensitivity of RT-PCR. The "ZEN" moiety is shown as in the probe at an illustrative location but can be positioned elsewhere in the probe, as desired. This probe can be used as an agent for detecting DENND1A Variant 2 mRNA or cDNA by hybridization to it, or it can be used, for instance, as a labeled probe that emits a detectable signal that is quenched during an assay such as RT-PCR.

The method of the invention includes in certain embodiments separating DENND1A Variant 2 mRNA from the biological sample, and mixing the separated DENND1A Variant 2 mRNA in a reaction container with non-naturally occurring reagents, including but not necessarily limited to synthetic oligonuclcotide primers and/or probes. Additional reagents that can be added into the reaction mixture include but are not limited to salts, buffers and the like, a recombinant prokaryotic or bacteriophage DNA polymerase, free nucleoside triphosphates, etc.

In certain embodiments, testing a biological sample comprising or which could comprise DENND1A Variant 2 mRNA includes amplification of the DENND1A Variant 2 mRNA using a machine, such as a thermocycler, which subjects nucleic acids in the sample to successive rounds of heating (melting) and cooling to facilitate a PCR-based amplification of the mRNA into its cognate cDNA, or a segment thereof. Thus, in certain embodiments, the invention involves creating and/or testing a cDNA or a cDNA segment from DENND1A Variant 2 mRNA.

In certain embodiments, assaying of DENND1A Variant 2 is performed directly in cells or tissues, such as by immunohistochemical methods or in situ hybridizations.

In other embodiments, the DENND1A Variant 2 protein can be detected using any suitable technique or reagent, and will generally entail separating the DENND1A Variant 2 protein from the biological sample and reacting the separated protein with at least one specific DENND1A Variant 2 binding partner. Such binding partners can include but are not necessarily limited to antibodies, whether polyclonal or monoclonal, and antibody fragments that can specifically hind to the DENND1A Variant 2 protein, such as Fab fragments, Fab' fragments, F(ab')$_2$ fragments, Fd fragments, Fv fragments, and scFv fragments. Other DENND1A Variant 2 specific binding partners can include aptamers, diabodies, or any other reagent that can specifically recognize DENND1A Variant 2 protein. Detecting a complex of a specific binding partner and DENND1A Variant 2 protein can be performed using any suitable technique, including Western blotting, and other immunodetection methods, such as enzyme linked immunosorbant assay (ELISA), a lateral flow test, such as a urine or blood testing strip, and the like.

In certain embodiments, the invention includes use of binding partners that can distinguish the DENND1A Variant 2 protein from DENND1A Variant 1 protein by, for example, detecting these proteins after they have been separated from one another based on their size and/or mobility. In one illustrative embodiment, we used a monoclonal antibody (mAb) purchased from Aviva Systems Biology. The mAb is specific for the N-termini of DENND1A Variants 1 and Variant 2, and it accordingly can recognize each of these proteins, but can differentiate between them when they are separated based on their respective amino acid content. In particular, the DENND1A Variant 1 protein has an approximate size of 110 kD whereas the DENND1A Variant 2 protein has an approximate size of 62 kD. Thus, they can be distinguished from one another using a mAb in a variety of immune-detection methods, including but not necessarily limited to Western blotting.

In other embodiments, the invention can detect/quantitate DENND1A Variant 2 protein using a binding partner that is directed to one or more epitopes in its unique 33 amino acid C-terminus. The 33 amino acid sequence that is unique between DENND1A Variants 1 and 2 is: NTIATPATLHILQKSITHFAAKFPTRGW TSSSH (SEQ ID NO: 10). We have employed polyclonal antibodies which are directed to a segment of this unique DENND1A Variant 2 C-terminal amino acid sequence. Specifically, we used DENND1A Variant 2 polyclonal antibody (rabbit) targeted to the following unique 15 amino acid sequence segment: QKSITHFAAKFP TRGWTSSSII (SEQ ID NO:11). We have utilized these polyclonal antibodies to detect DENND1A Variant 2 protein and have detected the same protein as obtained with the N-terminal antibody described above. The 15 amino acid sequence segment was chosen based on our analysis that predicted it to be optimally antigenic, and unlikely to result in production of antibodies that would have non-specific cross-reactivity with other proteins.

If desired, the determination of DENND1A Variant 2 mRNA and/or protein can be compared to a reference. The reference to which the Variant 2 mRNA and/or protein levels from the individual can be compared can be any suitable reference, examples of which include but are not limited to samples obtained from individuals who do not have the particular condition for which a diagnosis is sought, such as PCOS. Such references can include matched controls (i.e., matched for age, sex, or other demographics), a standardized curve(s), and/or experimentally designed controls such as known input RNA or protein used to normalize experimental data for qualitative or quantitative determination of the DENND1A Variant 2 from the sample for mass, molarity, concentration and the like. The reference level may also be depicted graphically as an area on a graph. In certain embodiments, determining Variant 2 mRNA and/or protein in a sample in an amount above a reference is a diagnosis of PCOS, or aids in a physician's diagnosis of PCOS. In certain embodiments, the reference is normal theca cells, which are compared to PCOS theca cells. In another embodiment, the reference is a sample that contains exosomes from an individual who does not have PCOS.

In certain embodiments, determining an increase in DENND1A Variant 2 mRNA of at least 1.5 fold in a sample as compared to a reference is a diagnosis of PCOS or aids in diagnosis of PCOS. In certain embodiments, the increase relative to a reference is at least 2.0, 3.0 or 4.0 fold, inclusive, and including all digits there between, and to the first decimal place.

In one aspect, the invention includes determining whether or not a subject is a candidate for receiving a prophylactic or therapeutic treatment for a condition that is positively correlated with DENND1A Variant 2 expression. In one embodiment the condition is PCOS. The method generally comprises testing a sample from the subject for the presence or absence or amount of DENND1A Variant 2. The presence of DENND1A Variant 2 or of an amount of DENND1A Variant 2 above a reference is indicative that the individual is a candidate for a prophylactic or therapeutic intervention for PCOS. In one embodiment, the method further comprises treating the individual for PCOS. The individual can be treated with any PCOS intervention, including but not limited to surgical interventions. Additional non-limiting examples of therapies include ovulation induction with clomiphene citrate or gonadotropins for women seeking to establish a pregnancy or oral contraceptive pills for women seeking symptomatic relief for manifestations of hyperandrogenemia. Weight loss or drugs like metformin can be used to treat metabolic features of PCOS.

In another aspect, the invention includes monitoring treatment of patient for a condition that is positively correlated with DENND1A Variant 2 expression. In one embodiment the condition is PCOS. The method comprises optionally testing a sample from the individual to establish the presence and/or amount or other value for DENND1A Variant 2 expression at the mRNA and/or protein level, and accordingly provides an initial DENND1A Variant 2 expression value. During or subsequent to treatment, the method comprises obtaining and testing a sample from the individual to establish the presence and/or amount or other value for DENND1A Variant 2 expression at the mRNA and/or protein level, and accordingly provides a treatment value. The treatment value can be determined over multiple time points. A reduction in the treatment value (i.e., a reduction in DENND1A Variant 2 mRNA or protein) relative to the initial value, and/or a reduction over the course of treatment is considered to be indicative that the treatment is effective. A lack of change for the treatment value relative to an initial value or to treatment values over time is indicative that the treatment is not effective, and/or that an alternative treatment should be considered.

In one embodiment, the invention provides a closed or sealed package or container that contains compositions useful for testing biological samples for DENND1A Variant 2 mRNA or protein. The compositions can include primers or probes as have been further described herein, and can include reagents used for hybridization of the probes or primers for nucleic acid amplification or for direct nucleic acid detection, for protein extraction and testing, and can include reagents for processing of a biological sample, such as for processing of liquid biological samples that could contain DENND1A Variant 2 mRNA or protein. In certain embodiments, the package can comprise one or more closed or sealed vials, bottles, or any other suitable containers or packaging comprising reagents, and which are designed for the sale, or distribution, containment, or use of the reagents. In addition to the reagents for detecting DENND1A Variant 2 mRNA or protein, the package can contain printed information. The printed information can be provided on a label, or on a paper insert, or printed on the packaging material itself. The printed information can include information that identifies the contents of the package, an indication of what marker the reagents are intended to detect and/or what condition the marker is related to, such as PCOS, and instructions for using the contents of the package for testing. In certain embodiments, the packages are considered to be kits.

In various embodiments, the invention comprises fixing in a tangible medium the result obtained by testing for DENND1A Variant 2 mRNA or protein. The tangible medium can be any type of tangible medium, such as any type of digital medium, including but not limited to a DVD, a CD-ROM, a portable flash memory device, or a printed or digitized report, etc., such as a spreadsheet or word processing document. The invention includes providing the tangible medium to a health care provider to assist with development of a diagnosis and/or recommendation for treatment of the individual and/or for developing a prognosis for the individual, such as for treating PCOS.

The following description and specific Examples are provided to illustrate the invention, but are not intended to be limiting in any way. Example 10 provides an expanded description of materials and methods used to obtain the data as further described below by way of Examples 1 through 9.

Example 1

Figure 1B:
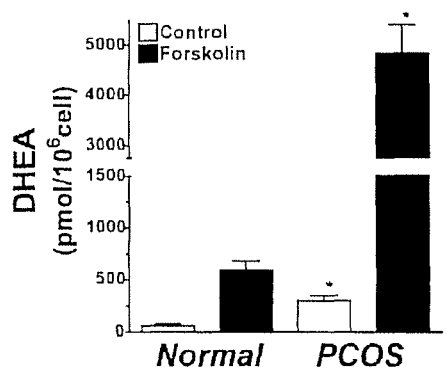

This Example provides data obtained from analysis of CYP17 mRNA accumulation and DHEA biosynthesis. FIGS. 1A and 1B provide graphical summaries of data which demonstrate that both basal and cAMP-stimulated CYP17 mRNA accumulation and DHEA production are increased in PCOS theca cells propagated in long-term culture. FIG. 1A shows that CYP17 mRNA abundance was evaluated in fourth passage theca cells that were isolated from 5 independent normal cycling women and 5 independent women with PCOS that were grown to subconfluence and transferred into serum free medium with vehicle, (Control conditions) or 20 µM forskolin (F). 16 h following treatment, mRNA was harvested, and CYP17 mRNA accumulation was measured using quantitative real-time PCR analysis. CYP17 mRNA values are normalized by TBP mRNA and are presented as relative abundance. As demonstrated by the data depicted in FIG. 1A, CYP17 mRNA accumulation was significantly increased in PCOS theca cells as compared to normal theca cells treated under basal and forskolin stimulated conditions (*, $P<0.05$). To evaluate whether androgen biosynthesis is increased in theca cells isolated from PCOS women as compared to normal cycling women, fourth passage theca cells isolated from multiple normal and PCOS women were treated in the presence or absence (Control) of 20 µM forskolin (F). Following 72 h of treatment, the media was collected, DHEA production was evaluated by ELISA, and the data were normalized to cell number. Results are presented as the mean ± SLUM of steroid levels from triplicate theca cell cultures from 4 independent normal and PCOS women. As shown in FIG. 1B, DHEA biosynthesis in PCOS theca cells was significantly increased under both basal and forskolin stimulated conditions (*, $P<0.05$).

Example 2

Figure 2:
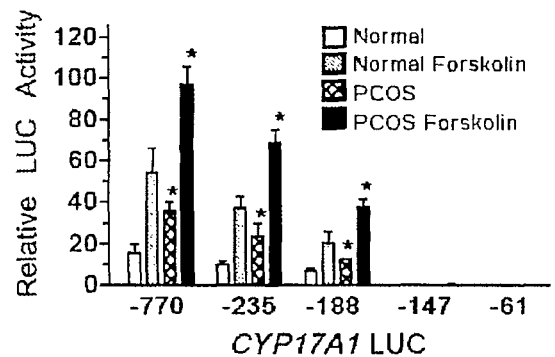
FIG. 2 provides a graphical representation of data obtained from deletion analysis of the CYP17A1 promoter in normal and PCOS theca cells and demonstrates that CYP17A1 promoter activity is increased in PCOS theca cells, under basal and forskolin-stimulated conditions (*, P<0.01), as compared to normal theca cells for individual promoter constructs.

This Example provides a description of data obtained from analysis of CYP17A promoter activity. To compare the transcriptional regulation of the CYP17A1 gene in normal and PCOS theca cells, cells were transiently transfected with pGL3 luciferase constructs containing −770, −235, −188, −147, or −61 to +44 bp of the 5'-flanking sequence of the CYP17A1 gene. All constructs contain the endogenous TATA box and transcriptional start site. Fourth passage theca cells from normal cycling and PCOS women were transiently transfected with the above constructs. Following transfection, cells were cultured in transfection medium alone or with forskolin (20 µM) for 24 h. Data are presented as relative luciferase (LUC) activity that was normalized with β-galactosidase activity, and represent the mean±SEM of independent experiments in 5 normal and 5 PCOS theca cell cultures. As shown in FIG. 2, CYP17A1 promoter activity was significantly increased in PCOS theca cells, under basal and forskolin-stimulated conditions (*, $P<0.01$), as compared to normal theca cells for individual promoter constructs.

Example 3

This Example provides data and a description of analysis of DENND1A mRNA accumulation in normal and PCOS cells and time course. The data from this analysis are summarized in FIGS. 3 and 4.

Figure 3A:
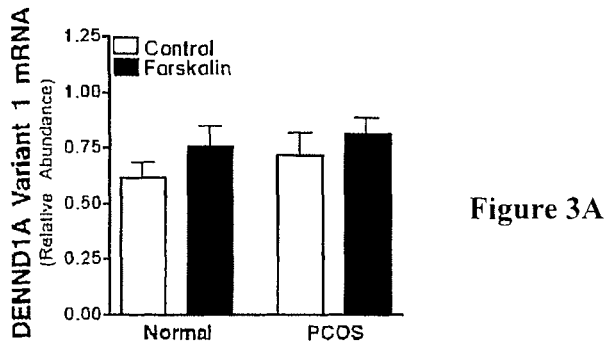
FIGS. 3A and 3B provide graphical representations of data demonstrating that DENND1A Variant 2 mRNA accumulation is greater in PCOS theca cells compared to normal theca cells.
Figure 3B:
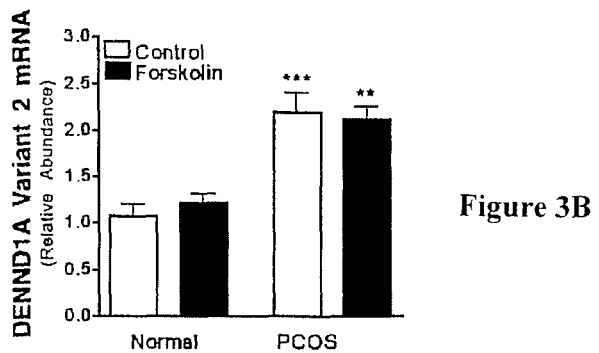

FIG. 3A shows that DENND1A Variant 1 mRNA is not differentially expressed in normal and PCOS theca cells. DENND1A Variant 1 and Variant 2 mRNA accumulation was quantitated in fourth passage theca cells isolated from 5 individual normal and 5 individual PCOS women that were grown in culture until subconfluence, then treated with and without 20 µM forskolin, an activator of adenylate cyclase for 16 h in serum free medium. Following treatment RNA was harvested and DENND1A Variant 1 (FIG. 3A) and Variant 2 (FIG. 3B) mRNA abundance was quantitated by Real-Time PCR analysis, and normalized using TBP mRNA abundance. The comparison of DENND1A Variant 1 mRNA accumulation normal and PCOS theca cells demonstrated no statistical difference in basal and forskolin-stimulated DENND1A Variant 1 mRNA accumulation in normal and PCOS theca cells (FIG. 3A). In contrast, DENND1A Variant 2 mRNA accumulation was significantly increased under both basal (*, P<0.01) and forskolin (, P<0.05) stimulated conditions in PCOS theca cells, as compared to normal cells (FIG. 3B).

Figure 4A:
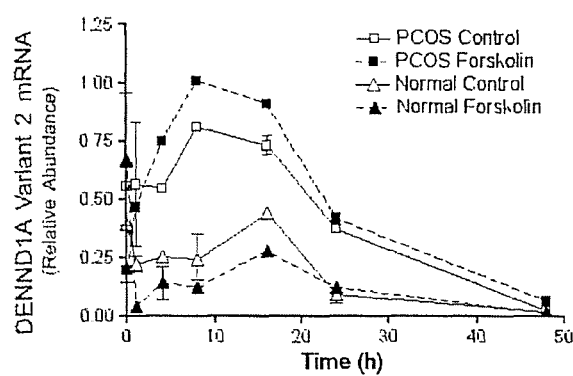
FIGS. 4A and 4B provide graphical representations of data demonstrating that DENND1A Variant 2 mRNA accumulation precedes CYP17 mRNA accumulation in normal and PCOS theca cells. The time courses of DENND1A Variant 2 (FIG. 4A) and CYP17 (FIG. 4B) mRNA accumulation was examined in normal and PCOS theca cells treated in serum free medium for 0, 4, 8, 16, 24, or 48 h in the presence and absence of 20 μM forskolin. Specifically, as shown in FIG. 4A, DENND1A.V2 mRNA accumulation increases rapidly between 4-8 h and plateaus around 16-20 h in PCOS cells (FIG. 4A). In contrast, CYP17 mRNA accumulation increases in response to forskolin treatment over 8-48 h. with ~2-3 fold increase in forskolin stimulated CYP17 mRNA in normal cells, and ~10-40 fold increase in PCOS cells (FIG. 4B).
Figure 4B:
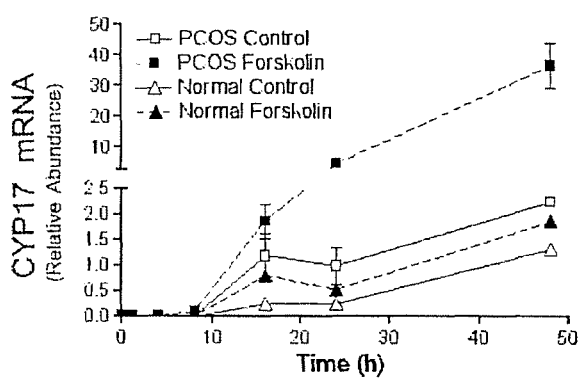

FIGS. 4A and 4B show that DENND1A Variant 2 mRNA accumulation precedes CYP17 mRNA accumulation in normal and PCOS theca cells. The time courses of DENND1A Variant 2 (FIG. 4A) and CYP17 (FIG. 4B) mRNA accumulation was examined in normal or PCOS theca cells treated in serum free medium for 0, 4, 8, 16, 24, or 48 h in the presence and absence of 20 µM forskolin. DENND1A Variant 2 and CYP17 mRNA abundance was measured using quantitative Real-Time PCR and normalized by TBP abundance. DENND1A.V2 mRNA accumulation increases rapidly between 4-8 h and plateaus around 16-20 h in PCOS cells (FIG. 4A). In normal cells, the same trend is observed, although it is less rapid and lower in magnitude. In agreement with the data in FIG. 3B. DENND1A.V2 mRNA accumulation is elevated ~2-3 fold in PCOS cells as compared to normal cells. In contrast. CYP17 mRNA accumulation increases in response to forskolin treatment over 8-48 h, with ~2-3 fold increase in forskolin stimulated CYP17 mRNA in normal cells, and ~10-40 fold increase in PCOS cells (FIG. 4B). The data presented in each of FIGS. 4A and 4B were obtained from 2 normal and 2 PCOS patients, that are representative of data collected from theca cells from 5 normal and 5 PCOS patients.

Example 4

This Example presents a characterization of the proteins encoded by DENND1A Variants 1 and 2 via Western Blot analysis. To evaluate DENND1A protein in human theca cells Western Blot analysis was performed in whole cell and nuclear extracts. To compare DENND1A protein expression in normal and PCOS theca cells, Western blot analysis was performed with 35 µg of whole cell extracts from theca cells isolated from multiple normal and PCOS patients treated with and without 20 µM forskolin for 24 h. From the results of these experiments we expected bands at approximately 110 kD, corresponding to DENND1A Variant 1, and at approximately 62 kD corresponding to DENND1A Variant 2. As shown in FIG. 5A, representative Western Blot analysis demonstrates increased 62 kD DENND1A Variant 2 (DENND1A.V2) in PCOS theca cells. In Figure SB, comparison of 25 µg of whole cell extracts and nuclear extracts from PCOS theca cells treated with and without 20 µM forskolin for 24 h, showed that 62 kD DENND1A Variant 2 was present in the nuclear component of PCOS theca cells. 110 kD DENND1A Variant 1 was not detected in normal or PCOS whole cell or nuclear extracts.

Example 5

This Example describes the effects of DENND1A Variant 2 expression on DHEA and CYP17 mRNA accumulation.

To examine the effects of DENND1A Variant 2 on DHEA biosynthesis and CYP17 mRNA accumulation we obtained a DENND1A.V2 expressing adenovirus from Applied Biological Materials, Richmond, BC.

DENND1A.V2 adenovirus (i.e., hDENND1A.V2-pAdenoG) was constructed by cloning DENND1A.V2 from pCMV6-XL4 plasmid encoding the DENND1A Variant 2 into pADenoG, from Origene, Rockville, Md. A control or Null adenovirus (Null-pAdenoG adendovirus, was also obtained from Applied Biological Materials. Richmond, BC.

Figure 6C:
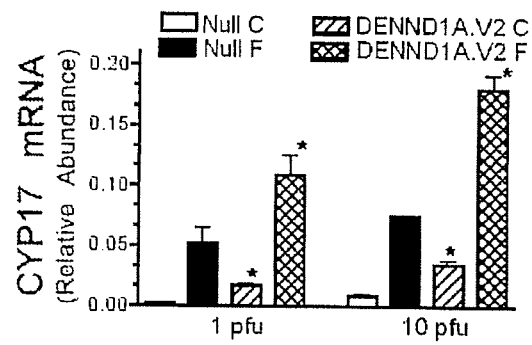

In these experiments 6-well plates of fourth passage normal theca cells were infected with 0.3, 1.0, 3.0, and 10 pfu/cell of either empty (Null) or DENND1A.V2 expressing adenovirus, treated with or without 20 µM forskolin in serum free medium. Following 72 h treatment DHEA in the media was quantitated. As shown in FIG. 6A, infection with all doses of DENND1A.V2 adenovirus significantly increased forskolin-stimulated DHEA production (*. P<0.05) compared with control Null adenovirus (FIG. 6A). Subsequent infection of normal theca cells with 3.0 pfu of adenovirus expressing DENND1A.V2 showed a significant increase in forskolin stimulated DHEA biosynthesis (*, P<0.05) compared to Null infected cells (FIG. 6B). To examine the effects of DENND1A.V2 expression on CYP17 mRNA accumulation, 100 mm cultures of fourth passage normal theca cells were infected with 1.0 pfu/cell DENND1A.V2 adenovirus, or Null adenovirus, and treated with or without 20 µM forskolin for 16 h. Following treatment, RNA was harvested, and CYP17 mRNA abundance was quantitated using a single step Brilliant 111 Ultra Fast QRT-PCR protocol and normalized by TBP abundance. As shown in FIG. 6C, 10 pfu DENND1A.V2 adenovirus significantly increases CYP17 mRNA accumulation in normal cells, with and without forskolin stimulation (*, P<0.05), as compared to infection with Null adenovirus.

Example 6

This Example provides a description of the effects of DENND1A Variant 2 expression on CYP17A1 promoter regulation.

To examine the effects of DENND1A Variant 2 on CYP17A1 gene transcription, theca cells were transfected with CYP17A1 reporter gene constructs containing −770/+44 of the 5'-flanking regions of the human CYP17A1 gene fused to the luciferase. This construct was constructed by subcloning the 770/+44 (KpnI/NaeI) fragment of the CYP17A1 5' flanking sequence into the luciferase pGL3 basic vector (Promega Corp, Madison, Wis.).

Figure 6D:
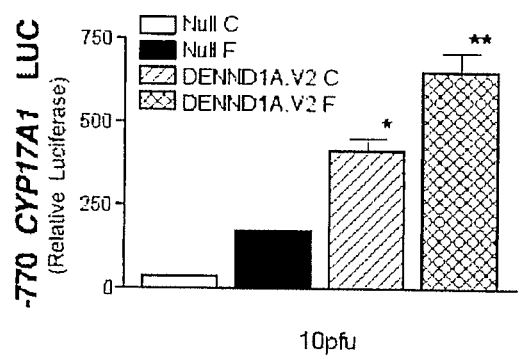

In these experiments fourth passage normal theca cells on 6-well plates were transfected using calcium phosphate in a 3% $CO_2$, 95% ambient air, 37 C incubator. The transfection reaction contained 2 µg/well of promoter luciferase plasmid, and 100 ng/well of plasmid, expressing β-galactosidase (used for normalization of transfection efficiency between replicates and transfection experiments). One hour following the transfection the cells were glycerol shocked in 15% glycerol and infected with the DENND1A.V2 (hDENND1A.V2-pADenoG) or Null-pAdenoG adenovirus, hDENND1A.V2-pADenoCG which were custom ordered from Applied Biological Materials, BC. One hour thereafter the cells were treated with serum-free medium with and without 20 µM forskolin, an activator of adenylate cyclase. 24 h thereafter the media was removed and the cells were frozen, resuspended in reporter lysis buffer (Promega, Madison, Wis.), and luciferase activity was determined utilizing the Luciferase Assay System (Promega. Madison, Wis.) on a Sirius Luminometer (Zylux Corp., TN), n-Gal activity was determined using a Galacto-Light Plus System (Applied Biosystems, Grand Island, N.Y.). Transfections were performed in triplicate, normalized using β-galactosidase, and calculated±SEM. The results of the experiments shown in FIG. 6D demonstrate that expression of DENND1A Variant 2 significantly stimulated both basal (*, P<0.05) and forskolin-stimulated (*, P<0.01) CYP17A promoter function in theca cells, compared to control plasmid. We believe these are the first data to suggest that DENND1A Variant 2 has the capacity to augment CYP17A1 gene expression in human theca cells.

Example 7

Figure 7A:
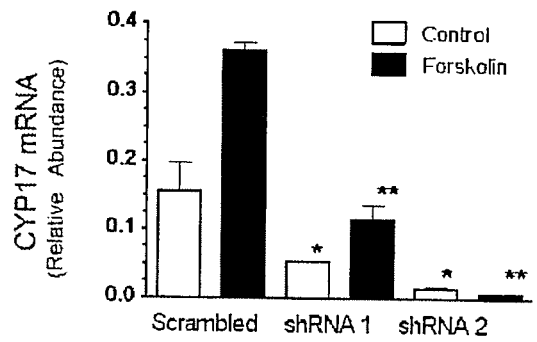
FIGS. 7A, 7B and 7C provide graphical representations of data demonstrating that knockdown of DENND1A Variant 2 in PCOS theca cells results in decreased CYP17A1 promoter regulation, CYP17 mRNA levels, and androgen biosynthesis.

This Example provides a description of the effects of DENND1A Variant 2 shRNA1 and shRNA2 retrovirus plasmids on CYP17 mRNA and CYP17A1 promoter regulation, as well as the effects of DENND1A Variant 2 shRNA lentivirus particles on DHEA biosynthesis. To investigate whether a reduction of DENND1A.V2 expression reduces elevated CYP17 mRNA in PCOS theca cells, silencing DENND1A.V2 shRNA retrovirus plasmids were transfected into PCOS theca cells and CYP17 message was assessed. PCOS theca cells were transfected with DENND1A.V2 shRNA retroviral plasmids and control plasmids from Origene, in pRSV (HUSH) retrovirus plasmids. The DENND1A retroviral shRNA1 plasmid was targeted to DENND1A.V2 sequence 5'-CGACGAGAGCTCGACCTC-TAC-3.' (SEQ ID NO:12). The DENND1A.V2 shRNA2 retrovirus plasmid was targeted to 5'-CCTCTTCATCACAT-TGACTTACG-3' (SEQ ID NO:13). Briefly, in these experiments fourth passage theca cells were transfected on 100 mm dishes with Genejuice transfection reagent (Novagen, Madison, Wis.) and 4 µg/dish empty expression vector or 4 µg/dish pRSV-Scrambled or plasmids specific to DENND1 1A Variant 2. i.e., pSV-shRNA1 or pRSV-shRNA2 in Optimen medium in a 3% CO2, 95% ambient air, 37 C incubator. Following 6 h transfection the cells were rinsed with PBS, and treated in serum-free medium with and without 20 µM forskolin an activator of adenylate cyclase. 24 h thereafter the media was removed and the cells were frozen, total RNA harvested, and CYP17 and TBP mRNA abundance was quantitated using a single step Brilliant III Ultra Fast QRT-PCR protocol. As shown in FIG. 7A. DENND1A.V2 shRNA1 and shRNA2 significantly inhibited both basal (*, $P<0.05$) and forskolin stimulated CYP17 mRNA accumulation (*, $P<0.01$) in PCOS theca cells.

Studies were performed to evaluate whether silencing shRNAs specific to DENND1A.V2 could reduce CYP17A promoter activity. To examine the effects of knockdown of DENND1A Variant 2 mRNA on CYP17A1 transcription, PCOS theca cells were transfected with CYP17A1 reporter gene constructs containing −235/+44 of the 5'-flanking regions of the human CYP17A gene fused to the luciferase. This construct was made by subcloning the −235/+44 (SacI/NaeI) fragment of the 5'flanking sequence of the CYP17A1 promoter into the luciferase pGL3 basic vector using pGL3 (Promega Corp., Madison, Wis.). In these experiments fourth passage theca cells were transfected with Genejuice transfection reagent (Novagen, Madison, Wis.) in Optimem medium in 12-well plates in a 3% CO2, 95% ambient air. 37 C incubator. The transfection reaction contained 250 ng/well of promoter luciferase plasmid, and 2.5 ng/well of pRL plasmid, expressing renilla (used for normalisation of transfection efficiency between replicates and transfection experiments). Scrambled pRV expression vector or plasmid encoding the DENND1A Variant 2 pRV-shRNA1 or pRV-shRNA2, romn Origene, Rockville, Mich.) was also added to the transfection reaction at 1 µg/well. Following 6 h transfection the cells were rinsed with PBS, and treated in serum-free medium with and without 20 µM forskolin as an activator of adenylate cyclase. 24 h thereafter the media was removed and the cells were frozen, resuspended in reporter lysis buffer (Promega, Madison, Wis.), and luciferase activity was determined utilizing the Dual Luciferase Assay System (Promega. Madison, Wis.) on a Sirius Luminometer (Zylux Corp., TN). Transfections were performed in triplicate, normalized using renilla, and calculated ±SEM.

Figure 7B:
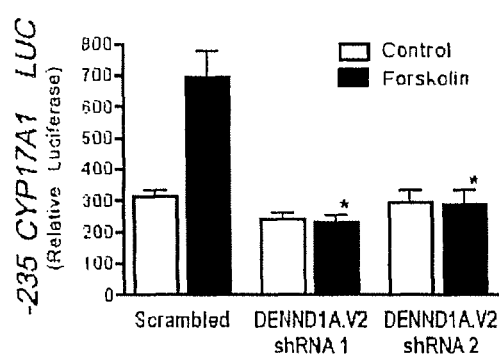

These experiments showed that co-transfection of PCOS theca cells with DENND1A.V2 shRNA1 or shRNA2 retrovirus plasmid resulted in a significant inhibition of forskolin-stimulated CYP17A) reporter activity (*, $P<0.05$), compared to Scrambled shRNA (FIG. 7B). The results from these experiments show that transfection of DENND1A Variant 2 shRNA1 and shRNA2 inhibit both basal and cAMP-dependent CYP17A1 reporter activity in PCOS theca cells, compared to scrambled shRNA. These data demonstrate that DENND1A Variant 2 confers increased transcriptional activation of CYP17A1 gene expression in PCOS theca cells.

Figure 7C:
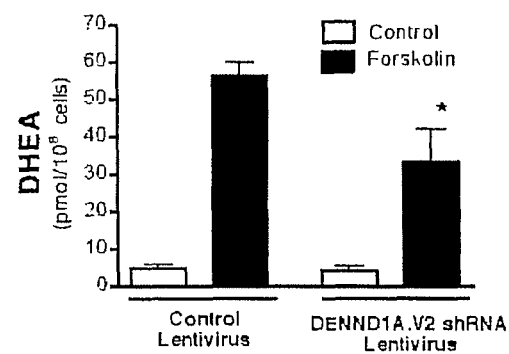

To evaluate the effect of knockdown of DENND1A.V2 on DHEA biosynthesis, PCOS theca cells were infected with a silencing shRNA DENND1A.V2 lentivirus or a control non-silencing lentivirus in the presence or absence of forskolin for 72 h as detailed above and with the following modifications. We utilized custom Thermo/Dharmacon GIPZ DENND1A.V2 shRNA particles. This shRNA lentivirus targets the mRNA equivalent of the DENND1A.V2 sequence 5'-CTCTTCATCACATTGACTT-3' (SEQ ID NO: 14). 100 mm tissue culture dishes of 50% confluent PCOS theca cells were infected with 300,000 particles of silencing shRNA DENND1A.V2 lentivirus or a control non-silencing lentivirus in serum free medium with 5 µg/mL polybrene in serum free medium. Six hours thereafter the lentivirus mixture was removed the cells were transferred into serum free medium in the presence or absence of forskolin for 72 h. As shown in FIG. 7C, infection with silencing shRNA DENND1A.V2 lentivirus significantly inhibited forskolin stimulated DHEA biosynthesis (*, $P<0.05$). Combined these data support that knockdown of DENND1A Variant 2 mRNA expression using shRNA/siRNA methodology results in inhibition of augmented CYP17A1 gene expression, CYP17 mRNA and androgen biosynthesis in PCOS theca cells.

Example 8

Figure 8A:
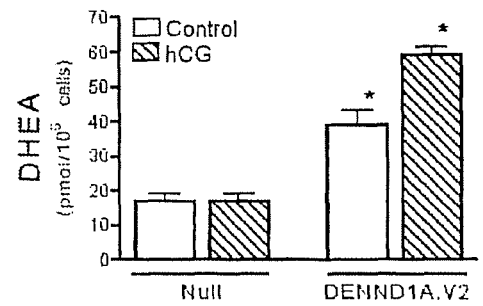
FIGS. 8A and 8B provide graphical representations of data demonstrating that DENND1A.V2 enhances LH/hCG-dependent changes in DHEA and CYP17A1 promoter regulation.
Figure 8B:
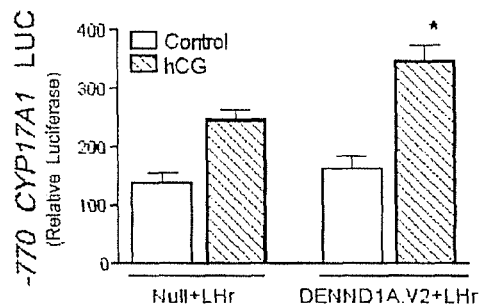

The Example demonstrates the effects of DENND1A Variant 2 on LH/hCG dependent changes on DHEA and CYP17A promoter activity. The data are summarized in FIGS. 8A and 8B. Briefly, to examine whether DENND1A.V2 affects LH/hCG-dependent DHEA biosynthesis, normal theca cells were infected with 3 pfu/cell Null or DENND1A.V2 adenovirus, and treated with and without 1.0 IU/mL hCG for 72 h. As shown in FIG. 8A, hCG had no significant effect on DHEA biosynthesis in Null treated cells. In contrast, DENND1A.V2 significantly increased DHEA biosynthesis (*, $P<0.05$) over control Null infected cells. DENND1A.V2 infection also significantly enhanced hCG-stimulated (*, $P<0.05$) DHEA biosynthesis (FIG. 8A). To examine whether DENND1A.V2 affects LH/hCG-dependent CYP17A expression, normal theca cells were transfected with the −770 CYP17A1 luciferase construct, then infected with 3 pfu/cell Null or DENND1A.V2 adenovirus. LHCGR expressing adenovirus (1.0 pfu/cell) was included in the infection to ensure that LH receptor was not limiting. Following transfection/infection, the cells were treated with and without 1.0 IU/mL hCG for 48 h. As shown in FIG. 8B, hCG-stimulated CYP17A1 promoter function is increased in DENND1A.V2 infected cells.

Example 9

Figure 9:
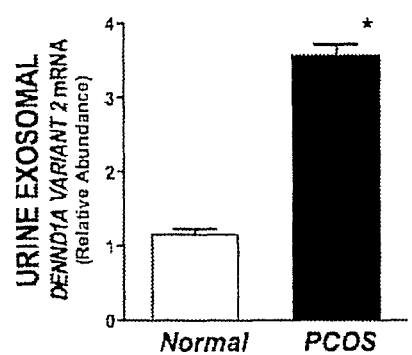
FIG. 9 provides a graphical representation of data demonstrating that DENND1A Variant 2 mRNA is increased in urine exosomes isolated from PCOS women as compared to urine exosomes from normal women. In particular, DENND1A Variant 2 mRNA is significantly increased in urine exosomes isolated from PCOS women (*, P<0.01), as compared to normal cycling women.

The Example demonstrates that the invention is suitable for detecting DENND1A Variant 2 in urine. In order to establish this, DENND1A Variant 2 mRNA abundance was compared in exosomal RNA isolated from urine from normal cycling and PCOS women. Mid-day urine samples were obtained from both populations of women, and were serially centrifuged at 300 g at 4 C for 10 minutes, 2000 g 4 C for 10 minutes, and 12,000 g at 4 C for 30 minutes. Exosomal RNA was then extracted from the supernatant using a modified protocol for, Urine exosome RNA Isolation, from Norgen, (Thoruld, CAN). DENND1A Variant 2 mRNA abundance was then quantitated using Real-Time PCR and normalized using 5S mRNA abundance. As shown in FIG. 9, DENND1A Variant 2 mRNA is significantly increased in urine exosomes isolated from PCOS women (*, P<0.01), as compared to normal cycling women. Thus, we have determined that the DENND1A Variant 2 can be detected in urine, and if desired can be compared to a reference to establish a positive correlation of the DENND1A Variant 2 in urine with PCOS.

Example 10

This Example provides a description of materials and methods used to conduct experiments described in the foregoing Examples.

Theca cell isolation and propagation. With respect to theca cell isolation and propagation for use in the Examples described below, for all of the experiments in which we obtained data from highly characterized normal and PCOS theca cells, isolated human ovarian tissue from individual follicles of normal cycling and PCOS women that have been isolated, banked, grown and passaged in long-term culture was used. Human theca internal tissue was obtained from follicles of women undergoing hysterectomy, following informed consent under an IRB protocol approved by the Institutional Review Board of the Pennsylvania State University College of Medicine. Individual follicles were dissected away from ovarian stroma, and dispersed with 0.05% collagenase I, 0.05% collagenase IA, and 0.01% deoxyribonuclease, in medium containing 10% fetal bovine serum (FBS), with antibiotics. The isolated follicles were size-selected for diameters ranging from 3-5 mm so that theca cells derived from follicles of similar size from normal and PCOS subjects could be compared. Theca cells were cultured on fibronectin coated dishes utilizing previously described growth medium (1:1 mixture of Dulhecco's Eagles Medium (DME) and Hams F-12 medium containing 5% FBS, 5% horse serum (HS), 2% UltroSer G, 20 nM insulin, 20 nM selenium. 1 µM vitamin E, and antibiotics). Sera and growth factors were obtained from the following sources: FBS and DME/F12 (Irvine Scientific, Irvine, Calif.): horse serum (Life Technologies, Grand Island, N.Y.); UltrSer G (Reactifs IBF, Villeneuve-la-Garenne, France): other compounds were purchased from Sigma (St. Louis, Mo.). The cells were grown in reduced oxygen tension (5% O2, 90% N2, and 5% CO2) and given supplemental antioxidants (vitamin E and selenium) to prevent oxidative damage.

Experiments comparing PCOS and normal theca were performed utilizing fourth passage (31-38 population doublings) theca cells isolated front size-matched follicles obtained from age-matched subjects. The use of fourth passage cells allowed us to perform multiple experiments from the same patient population, and were propagated from frozen stocks of second passage cells in the media described above. For all studies, theca cell cultures obtained from numerous independent patients were examined, for confirmation. The passage conditions and split ratios for all normal and PCOS cells were identical.

The PCOS and normal ovarian tissue came from age-matched women, 38-40 years old. The diagnosis of PCOS was made according to NIH consensus guidelines, which include hyperandrogenemia, oligoovulation, polycystic ovaries, and the exclusion of 21α-hydroxylase deficiency, Cushing's syndrome, and hyperprolactinemia. All of the PCOS theca cell preparations studied came from ovaries of women with fewer than six menses per year and elevated serum total testosterone or bioavailable testosterone levels. Each of the PCOS ovaries contained multiple subcortical follicles of less than 10 mm in diameter. The control (normal) theca cell preparations came from ovaries of fertile women with normal menstrual histories, menstrual cycles of 21-35 days, and no clinical signs of hyperandrogenism. Neither PCOS nor normal subjects were receiving hormonal medications at the time of surgery. Indications for surgery were dysfunctional uterine bleeding, endometrial cancer, and/or pelvic pain.

Quantitating DENND1A Variant 1, DENND1A Variant 2, and CYP17 mRNA. For those data presented below wherein mRNA is quantitated, the following materials and methods were used.

DENND1A Variant 1, DENND1A Variant 2, CYP17, TATA Box Binding Protein (TBP), and 5S Ribosomal RNA abundance were determined by quantitative Real-Time PCR utilizing the single step Brilliant III Ultra Fast QRT-PCR Master Mix (Agilent) using 100 µg total RNA/tube, final concentration of each forward and reverse primers we determined using the manufacturers specifications. The specific primer and probe sequences used are provided below in detail.

The DENND1A Variant 2 specific mRNA Primer and Probe set used was specific to the DENND1A 3'UTR sequence, the entire sequence of which is presented here beginning at nt 1914 (except for the polyA tail):

```
                                                        (SEQ ID NO: 15)
1914                                                           cttacgc 1921    cgttgctttt ccagactggg cagaggagct aacttcacaa tgtgtgccaa agagccggtg 1981    tctgataatc ccattttcct gcttatcacc tgaactgtgt cagtatcact tttagttttg 2041    ttggttggtt ggtttgttgt ttgtttaata tgccctgttt tctacttctg ttggaaaata 2101    tttggggttg aaataaacca gtgggagcat gg
```

To amplify the unique DENND1A 3'UTR described above, the following primers were used: Forward Primer (5'-GGGCTGACTTCGCAGTGTGT-3'-(SEQ ID NO:7); Reverse Primer (5-ACAGTTCAGGTGATAAGCAG-GAAA-3'-SEQ ID NO:8); Probe (5'/56-FAM/CCAAAA-GAC/LEN/CGG TOT CTGATAATCCCA/3IABKFQ/-3'-(SEQ ID NO:9)). (Position NM_024820.2, Forward 1951, Probe 1967, Reverse start 5'-2018). 200 nM primers and 200 nM probe used for the reaction. We selected these particular primer and probes sequences to mitigate the likelihood they would anneal to other mRNAs that could be present in the samples.

The DENND1A Variant 1 specific mRNA Primer and Probe set Forward Primer (5'-GGATICATTTCCATAAAC-CAAGTTAAA-3' SEQ ID NO:16) Reverse Primer (5'-CACAATTCCTGCGTGCTCA3' SEQ ID NO:17), Probe (5'/56-FAM/ATGGCCCOA/ZEN/CCATTT AAGAAAACAACCA/#IA3BkFQ/-3 SEQ ID NO: 18) (Position NM_024820.1, Forward 4434, Probe 4463, Reverse start 5'4513). 200 nM primers and 200 nM probe used for the reaction.

The CYP17 mRNA Primer and Probe set. Forward primer (5'-GGCCTCAAA TGGCAACTCTAGA-3' SEQ ID NO: 19): Reverse Primer (5'-CTTCTGATCGCCATCCTTGAA-3' SEQ ID NO:20): Probe (5' 6-FAM-TCGCGTC-CAACAACCGTAAGGGTATC-3' BHQ-1.3' SEQ ID NO:21). (Position NM_00012, Forward 328, Probe 391, Reverse start 5' 464). 200 nM primer and probe.

TATA-hox binding protein (TBP) mRNA Primer and Probe set. TRP was determined for each cDNA sample in theca cells for normalization. Forward Primer (5'-CACGGC ACTGATTTTCAGTTC-3' SEQ II) NO:22). Reverse Primer (5'-TCTTGCCTGCCAGTCTGGACT-3' SEQ ID NO:23), Probe (5'-JOE-TGTGCACACAGGAGCCAAGAGT-GAAGA-3' BHQ-1,3 SEQ ID NO:24').

5S Ribosomal RNA Primer and Probe set. 5S was determined for each cDNA sample in urine exosomal RNA for normalization. Forward Printer (5'-GCCTCCTTCAGCGTCTAC), Reverse Primer (5'GTCTCCCATCAAGTATAACC-3' SEQ ID NO:25 Probe (5"HEX-TCTCGTCTG/ZEN/ATCTCGGAAGCTAACCA-3'IABKFQ-1' SEQ ID NO:26). (Position X51545, Forward 262. Probe 306, Reverse start 5' 343). 50 nM primers and 50 nM probe used for the reaction.

The gene specific one step PCR was carried out in duplicate for each mRNA sample and for a series of serial dilutions in an Mx3000 Thermocycler system (Stratagene, Santa Clara, Calif.) according to manufacturers instructions for this instrument. An arbitrary value of RNA template was assigned to each serial dilution (ie, 1000, 300, 100, 30, 10, 3, 1, 0.3, 0.1 ng) and plotted against the Ct value (y-axis=Ct; x-axis=value, log scale) to generate a standard curve. Each unknown was assigned an arbitrary value based on the slope and y-intercept of the standard curve. The same process was carried out for TBP in order to use TBP values as a normalized template loaded into each reaction. The mean target value for each unknown was divided by the mean TBP value for each unknown to generate a normalized value for the target for each sample.

Method of RNA isolation from theca cells. Following treatment as indicated in serum free medium theca cells were flash frozen and stored at −80 C. Each 100 mm culture dish was harvested on ice in 500 μL trizol reagent (Sigma, St. Louis, Mo.). 100 μl of ultra pure chloroform was added to the triol/cell mixture, vortexed for ten seconds, then centrifuged for 30 min at 14,000 rpm in a 4 C refrigerated Eppendorf Centrifuge (Hauppauge, N.Y.). The centrifuged samples were placed on ice and the upper phase was placed in a fresh RNase free eppendorf tube with an equivalent amount of ice cold ultrapure isopropanol at −20 C overnight. The samples were then centrifuged for 30 min at 14,000 rpm in a 4 C refrigerated Eppendorf Centrifuge. The pellet was resuspended in 100 μl DEPC treated water, with 42 μL of 2M NaAC and 600 μL of ETOH then frozen at −80 C for 4-24 h. The samples were then centrifuged for 30 min at 14,000 rpm in a 4 C refrigerated Eppendorf Centrifuge (Hauppauge, N.Y.), rinsed with 70% ETOH, air dried, and resuspended in 50 μl of DEPC on ice. RNA was quantitated using a spectrophotometer at 260/280 or on a NanoDrop device. Samples usually have a 260/280 ratio above 1.60. CYP17, DENND1A.V2 and DENND1.V1 mRNA abundance were quantitated as described by quantitative Real-Time PCR using the Agilent One Step Brilliant III Kit, and normalized by TBP or 5S abundance.

Method of Measurement of Androgen/DHEA Biosynthesis. Following treatment of theca cells in 6-well culture plate as described in serum free medium the medium was collected and frozen and stored at −20 C. Each of treated 6-wells was rinsed with PBS, trypsinized, and counted twice with a Beckman Z2 Coulter Counter, Brea Calif. DHEA accumulation into the medium was quantitated using an ELISA platform (DRG International Incorporated, Springfield, N.J.).

Methodology for Western Analysis of DENND1A Protein in Normal and PCOS Theca Cells. To examine and compare DENND1A protein was examined in normal and PCOS theca cells, fourth passage theca cells were grown until subconfluent and transferred into serum free medium with and without forskolin for 24 hours. Following treatment, for whole cell lysates, theca cells were harvested in ice cold modified RIPA buffer (30 mM Tris, 150 mM NaCL, 50 mM Na F, 0.5 mM EDTA, 0.5% deoxycholic acid. 1.0% Nonident P-40, 0.1% SDS) containing 1 mM sodium otnhovanadate, 0.5 mM phenymethylsufonyl fluoride. 1 mM dithiothreitol, 1.0 mM benzamidine, 1 μM microcystin, 2 μg/ml leupeptin, and 2 μg/ml pepstatin A. For isolation of nuclear extracts, cells were harvested with trypsin/EDTA and cytoplasmic extracts were prepared in buffer containing 0.1% NP-40, 20 mM HEPES (pH 7.9). 20 mM sodium chloride. The nuclear pellet was centrifuged at 10,000 g for 5 min, and nuclear extracts were prepared in buffer containing 20 mM HEPES. 25% glycerol, 500 mM sodium chloride, 1.5 mM magnesium chloride. Both buffers also contained 1 mM dithiothreitol, 0.5 mM PMSF, 0.2 mM EDTA, 2 μg/mL leupeptin, 1 mM benzamidine, 1 mM sodium orthovanadate, and 20 mM sodium fluoride to inhibit protein phosphatases and proteases. Protein concentrations of whole cell extracts (WCE) determined using a Bio-Rad DC protein assay (Hercules, Calif.). Protein samples of nuclear extracts (NE) were separated on a 10% SDS-PAGE, transferred to PVDF membrane, and Western analysis was performed using Abcam antibody specific for the N-terminal sequence of DENND1A, and was visualied using ECL (Pierce). From the results of these experiments we expected bands at approximately 110 kD, corresponding to DENND1A Variant 1, and an approximate 62 kD corresponding to DENND1A Variant 2, given that the N-terminal antibody purchased is to the common N-terminal peptide, PGVSVHLSV HSYFFVPDTRELPSIPENRNLTEYFVAVDVNNMLH-LYASML (SEQ ID NO:27) sequence that begins amino acid #13 of both DENND1A Variant 1 and 2 peptides.

Method for Isolation of Urine Exosomal mRNA. Exosomes are small vesicles of about 40-100 nm originating from within multi-vesicular bodies, that are secreted from cells into extra-cellular fluid, and are found in different bodily fluids such blood, blood derivatives, urine, and amniotic fluid. Exosomes are produced by all cell types, and have a molecular phenotype which largely reflects that of the parent cell. Their contents reflect the origin and the physiological status of the source cells, and thus exosomal RNAs can serve as biomarkers for various diseases.

Urine samples were obtained from normal women and women with PCOS, using the same clinical criteria described above, following informed consent under an IRB protocol approved by the Institutional Review Board of the Pennsylvania State University College of Medicine. The urine samples were collected and placed at 4 C until processed. The urine samples were then aliquoted into 15 ml tubes and centrifuged in a swing bucket in a Sorvall Super T21 Table Top Centrifuge at 300 g at 4 C for 10 minutes to remove particulate matter. The supernatant was transferred to a new tube and centrifuged at 2000 g 4 C for 10 minutes in the same centrifuge to clear cellular debris. The supernatant was transferred to a 17×100 mm culture tube and centrifuged at 12,000 g at 4 C for 30 minutes using a floor Beckman Coulter Avanti J-E Centrifuge. The supernatant was then transferred to 15 ml tube, and the sample was either frozen at −80 C until use, or exosomal RNA was extracted using a modified protocol of the "Urine Exosome RNA Isolation Kit" from Norgen (Thorold, CAN).

Using the Norgen Kit, 10 ml of the centrifuged urine was added to a fresh 15 cc conical tube on ice. 300 µl of Solution A1 and 250 µl of Solution A2 was added to each tube. The tubes were vortexed well for 10 seconds. Using the table top Sorvall Centrifuge, the tubes/samples were spun at 3200 rpm 4 C for 2 minutes. The supernatant was aspirated off, and the tubes/pellets were placed on ice. The pellet was resuspended in 300 µl of Solution B, and incubated at room temperature for 5 minutes, and on ice for 10 minutes. 300 µl of ice cold 67% Isopropanol was added to the mixture, and vortexed well for 10 seconds. The lysate was transferred to a mini filter spin column, provided by the kit with a collection tube. The lysate/column was spun in a table top microfuge at 14,000 rpm 4 C for 1 minute, and the flow through was discarded. 400 µl ice cold Wash Solution was added to the reassembled spin column, and centrifuged again at 14,000 rpm 4 C for 1 minute. The flow through was discarded, another 400 µl Wash Solution was applied and spun again at 14,000 rpm 4 C for 1 minute. The flow through was discarded, 400 µl Wash solution was applied (3 total washes) and spun at 14,000 rpm 4 C for 4 minutes. The collection tube with the flow through was discarded, and the spin column was placed in an elution tube. 50 µl of sterile dH$_2$O was added to the spin column and spun at 2,000 rpm 4 C for 2 minutes, followed by a 14,000 rpm 4 C spin for 2 minutes. Another 50 µl sterile dH$_2$O was added to the spin column, and again spun at 2.000 rpm 4 C for 2 minutes, followed by a 14,000 rpm 4 C spin for 2 minutes. The spin columns were discarded; the elution tubes were capped and spun a final time at 14.000 rpm 4 C for 10 minutes to pellet any remaining resin from the column. The supernatant/RNA was then transferred to new 1.5 ml tubes. Nucleic acid content was quantitated using a NanoDrop Spectrophotometer, the samples were then aliquoted into the desired ng/µl and frozen at −80 C.

While the invention has been described through specific embodiments, routine modifications will be apparent to those skilled in the art and such modifications are intended to be within the scope of the present invention.

What is claimed is:

1. A method for polycystic ovary syndrome diagnosis, the method comprising the steps of:
    measuring an amount of DENND1A Variant 2 protein in a biological sample from a subject, wherein measuring the amount of DENND1A Variant 2 protein is performed using a composition comprising antibodies, wherein the antibodies are bound to the DENND1A Variant 2 protein, wherein the binding of the antibodies to the DENND1A Variant 2 protein is detected, and wherein the antibodies specifically recognize at least one epitope in a segment of the DENND1A Variant 2 protein consisting of the 33 amino acids at its C-terminus, wherein the DENND1A Variant 2 protein is contacted with the antibodies and wherein antibodies bound to the segment are detected;
    comparing the amount of DENND1A Variant 2 protein to a reference value; and
    diagnosing said subject with polycystic ovary syndrome when said amount of DENND1A Variant 2 protein is increased as compared to the reference value.

2. A method for selecting an individual as a candidate for therapy for polycystic ovary syndrome, the method comprising the steps of:
    measuring an amount of DENND1A Variant 2 protein in a biological sample from said individual, wherein measuring the DENND1A Variant 2 protein is performed using a composition comprising antibodies, wherein the antibodies are hybridized bound to the DENND1A Variant 2 protein, wherein the binding of the antibodies to the DENND1A Variant 2 protein is detected, and wherein the antibodies specifically recognize at least one epitope in a segment of the DENND1A Variant 2 protein consisting of the 33 amino acids at its C-terminus, wherein the DENND1A Variant 2 protein is contacted with the antibodies and wherein antibodies bound to the segment are detected;
    diagnosing said individual with polycystic ovary syndrome when said amount of DENND1A Variant 2 protein is increased as compared to the reference value; and
    designating the individual diagnosed with polycystic ovary syndrome as a candidate for the polycystic ovary syndrome therapy.

3. The method of claim 1, wherein the biological sample is selected from a sample comprising urine, blood, plasma, serum or saliva.

4. The method of claim 2, wherein the biological sample is selected from a sample comprising urine, blood, plasma, serum or saliva.

* * * * *